United States Patent [19]

Yuan et al.

[11] Patent Number: 5,728,521
[45] Date of Patent: Mar. 17, 1998

[54] TARGETED CLEAVAGE OF RNA USING EUKARYOTIC RIBONUCLEASE P AND EXTERNAL GUIDE SEQUENCE

[75] Inventors: Yan Yuan; Cecilia Guerrier-Takada, both of New Haven; Sidney Altman, Hamden; Fenyong Liu, New Haven, all of Conn.

[73] Assignee: Yale University, New Haven, Conn.

[21] Appl. No.: 215,082

[22] Filed: Mar. 18, 1994

Related U.S. Application Data

[63] Continuation-in-part of Ser. No. 207,547, Mar. 7, 1994, Pat. No. 5,624,824, which is a continuation-in-part of Ser. No. 54,892, Apr. 28, 1993, abandoned, which is a continuation-in-part of Ser. No. 931,937, Aug. 18, 1992, abandoned, which is a continuation-in-part of Ser. No. 875,099, Apr. 28, 1992, abandoned, which is a continuation-in-part of Ser. No. 568,834, Aug. 17, 1990, Pat. No. 5,168,053, which is a continuation-in-part of Ser. No. 328,368, Mar. 24, 1989, abandoned.

[51] Int. Cl.$^6$ .............................. C12Q 1/68; C12P 19/34
[52] U.S. Cl. .................................... 435/6; 435/91.2
[58] Field of Search ......................... 435/6, 172.1, 91.1, 435/91, 31, 172.3, 199, 320.1, 948, 5, 91.2; 514/44; 536/23.1, 23.2, 24.5; 424/93.2

[56] References Cited

U.S. PATENT DOCUMENTS

| | | | |
|---|---|---|---|
| 4,868,116 | 9/1989 | Morgan et al. | 435/240.2 |
| 4,980,286 | 12/1990 | Morgan et al. | 435/172.3 |
| 4,987,071 | 1/1991 | Cech et al. | 435/91 |
| 5,168,053 | 12/1992 | Altman et al. | 435/91 |

FOREIGN PATENT DOCUMENTS

| | | |
|---|---|---|
| WO88/04300 | 6/1988 | WIPO . |
| WOI 88/04300 | 6/1988 | WIPO . |
| WO 89/05852 | 6/1989 | WIPO . |
| WO8905852 | 6/1989 | WIPO . |
| PCT/US89/ 03794 | 3/1990 | WIPO . |
| 9322434 | 11/1993 | WIPO . |

OTHER PUBLICATIONS

Guerrier-Takada, et al., *Cell* 35, 849 (1983).
Guerrier-Takada, et al., *Science* (1984) vol. 223, pp. 285–286.
McClain, et al., *Science* 238, 527–528 (1987).
Altman, et al., *Gene* 82, 63–64 (1989).
Guerrier-Takada, et al., *Science* 246, 1578–1584 (1989).
Baer, et al., *Nucleic Acids Research* 18 (1), 97–103 (1989 or 1990).
Lee, et al., *Mol. Cell. Biol.* 9(6), 2536–2543 (Jun. 1989).
Pace, et al., *Gene* 82, 65–75 (1989).
Pace, et al., *J. Biol. Chem.* 265(7), 3587–3590 (1990).
Altman, *Advances in Enzymology,* edited by A. Meister, vol. 62, pp. 1–36 (J. Wiley & Sons 1989).
Surratt, et al., *Molecular Biology of RNA,* 79–88 (Alan R. Liss, Inc., 1989).

Altman, S., et al., "Catalysis by the RNA subunit of RNase P—a minireview," *Gene* 82:63–64 (1989).
Altman, *J. Biol. Chem.* 265:20053–20056 (1990)*.
Altman, Sidney, "Ribonuclease P: An Enzyme with a Catalytic RNA Subunit," *Advances in Enzymology* ed. Alton Meister, 62:1–36 (John Wiley & Sons 1989).
Baer, Madeline, et al., "Structure and transcription of a human gene for H1 RNA, the RNA component of human RNase P," *Nucleic Acids Research* 18:97–103 (1989).
Beaudry and Joyce, *Science* 257:635 (1992)*.
Berzal–Heranz, et al., *Genes and Dev.* 6:129 (1992)*.
Bartkiewicz, et al., *Genes and Dev.* 3:488–499 (1989)*.
Branch and Robertson, *Science* 233:450–455 (1984)*.
Branch, Andrea D., et al., "An Ultraviolet–Sensitive RNA Structural Element in a Viroid–Like Domain of the Hepatitis Delta Virus," *Science* 243:649–652 (1989).
Kruger, Kelly, et al., "Self–Splicing RNA: Autoexcision and Auto–cyclization of the Ribosomal RNA Intervening Sequence of Tetrahymena" *Cell* 31:147–157 (1982).
Chowrira, et al., *Nature* 354:320 (1991)*.
Das, et al., *EMBO* 7:503–512 (1988)*.
Doersen, et al., *J. Biol. Chem.* 260:5942 (1985)*.
Forster, Anthony C., and Sidney Altman, "External Guide Sequences for an RNA Enzyme," *Science* 249:783–786 (1990).
Forster and Symons, *Cell* 50:9–16 (1987)*.
Green, et al., *Nature* 347:406 (1990)*.
Guerrier–Takada, Cecilia, et al., "Specific Interactions in RNA Enzyme–Substrate Complexes," *Science* 246:1578–1584 (1989).
Sharmeen, et al., *J. Virol.* 62:2674–2679 (1988)*.
Surratt, Christopher K., et al., "Processing of a Synthetic tRNA Precursor Model by *E. coli* RNase P and M1 RNA," *Molecular Biology of RNA* 79–88 (Alan R. Liss, Inc. 1989).
Tuerk and Gold, *Science* 249:505 (1990)*.
Uhlenbeck, *Nature* 324:429–433 (1987)*.

(List continued on next page.)

*Primary Examiner*—Eggerton A. Campbell
*Attorney, Agent, or Firm*—Arnall Golden & Gregory, LLP

[57] ABSTRACT

It has been discovered that any RNA can be targeted for cleavage by RNAase P from eukaryotic cells, for example, human RNAase P, using a suitably designed oligoribonucleotide ("external guide sequence", or EGS) to form a hybrid with the target RNA, thereby creating a substrate for cleavage by RNAase P in vitro. The EGS hydrogen bonds to the targeted RNA to form a partial tRNA like structure including the aminoacyl acceptor stem, the T stem and loop, and part of the D stem. The most efficient EGS with human RNAase P is the EGS in which the anticodon stem and loop was deleted. Modifications can also be made within the T-loop. Methods are also disclosed to randomly select and to express a suitable EGS in vivo to make a selected RNA a target for cleavage by the host cell RNAase P, thus preventing expression of the function of the target RNA. The methods and compositions should be useful to prevent the expression of disease-causing genes in vivo.

7 Claims, 8 Drawing Sheets

OTHER PUBLICATIONS

Wagner, et al., *Proc. Natl. Acad. Sci.* 78:1441–1445 (1981)*.

Wigler, et al., *Proc. Natl. Acad. Sci. USA* 76:1373–1376 (1979)*.

Wu, Huey-Nan and Michael M. C. Lai, "Reversible Cleavage and Ligation of Hepatitis Delta Virus RNA," *Science* 243:652–655 (1989).

Yuan, Yan, et al., "Targeted cleavage of mRNA by human RNase P," *Proc. Natl. Acad. Sci.* 89:8006–8010 (1992).

Guerrier-Takada, Cecilia and Sidney Altman, "Catalytic Activity of an RNA Molecular Prepared by Transcription in vitro," *Science* 223:285–286 (1984).

Guerrier-Takada, Cecilia et al., "The RNA Moiety of Ribonuclease P is the Catalytic Subunit of the Enzyme," *Cell* 35:849–857 (1983).

Hansen, et al., *Gene* 38:535 (1987)*.

Lawrence, Nathan P. and Sidney Altman, "Site-directed Mutagenesis of M1 RNA, the RNA Subunit of *Escherichia coli* Ribonuclease P," *J. Mol. Biol.* 191:163–175 (1986).

Lee, Jae-Yong and David R. Engelke, "Partial Characterization of an RNA Component That Copurifies with *Saccharomyces cerevisiae* RNase P," *Molecular and Cellular Biology* 9(6): 2536–2543 (1989).

Li, Ying, et al., "Targeted cleavage of mRNA in vitro by RNase P from *Escherichia coli*" *Proc. Natl. Acad.* 89:3185–3189 (1992).

McClain, William H., et al., "Model Substrates for an RNA Enzyme," *Science* 238:527–530 (1987).

Mills, Donald R., et al., "Qβ Replicase: Mapping the Functional Domains of an RNA-dependent RNA Polymerase," *J. Molecular Biology* 205:751–764 (1988).

Pace, Norman R., et al., "Phylogenetic Comparative analysis and the secondary structure of ribonuclease P RNA—a review," *Gene* 82:65–75 (1989).

Pace, Norman R., et al., "Ribonuclease P: Function and Variation," *J. of Biol. Chem.* 265(7):3587–3590 (1990).

Perreault and Altman, *J. Mol. Biol.* 226:399–409 (1992)*.

Pyle, et al., *Proc. Natl. Acad. Sci. USA* 87:8187–8191 (1990)*.

Roizman, *Cell* 16:481–494 (1979)*.

Rossi, J., et al., *J. Cell. Biol.* (Suppl. 14A, D428) (1990).

Sarver, Nava, et al., "Ribozymes as Potential Anti-HIV-1 Therapeutic Agents," *Science* 247:1222–1225 (1990).

Li et al. PNAS 89:3185–3189 (1992).

Lawrence et al. J. Mol. Biol. 191:163–175 (1986).

Baer et al. NAR 18:97–103 (1989).

Rossi et al. J. Cell. Biochem. (Suppl. 14A, D428) (1990).

Sarver et al. Science 247: 1222–1225 (1990).

Sampson et al. (1987), Cold Spring Harbor Symp. Quant. Biol., vol. 52, pp. 267–275.

Yuan et al PNAS 89:8006–8010 (1992).

Biosis Abstract Jan. 17, 1994 Biotechnology Newswatch, p. 8.

Crystal et al. "Transfer of Genes to Humans Early Lessons and Obstacles to Success" Science 270 (1995), 404–410, Oct. 1995.

Johnston et al. "Present Status and Future Prospects for HIV Therapies" Science 260 (1993), 1286–1292, May 1993.

Whitton "Antisens Treatment of Viral Infection" Adv. Viral Res. 44 (1994), 267–303, 1994.

Joyce "Amplification, mutation and selection of catalytic RNA" Gene 82: 83–87, 1989.

Baer et al. "Structure and transcription of a human gene for H1 RNA . . . " Nucleic Acids Res. 18: 97–103, 1989.

EGS 104 + TK mRNA

EGS 109 + TK mRNA

EGS 112 + TK mRNA

TARGETED CLEAVAGE OF RNA USING EUKARYOTIC RIBONUCLEASE P AND EXTERNAL GUIDE SEQUENCE

This application is a continuation-in-part of U.S. Ser. No. 08/207,547, filed Mar. 7, 1994 U.S. Pat. No. 5,624,824, which is a continuation-in-part of U.S. Ser. No. 08/054,892, filed Apr. 28, 1993, which is a continuation-in-part of U.S. Ser. No. 07/931,937 filed Aug. 18, 1992, now abandoned, which is a continuation-in-part of U.S. Ser. No. 07/875,099 filed Apr. 28, 1992, now abandoned, which is a continuation-in-part of U.S. Ser. No. 07/568,834, filed Aug. 17, 1990, now U.S. Pat. No. 5,168,053, which is a continuation-in-part of U.S. Ser. No. 07/328,368, filed Mar. 24, 1989, now abandoned.

The United States government may have certain rights in this invention as a result of grants from the National Institutes of Health and National Science Foundation, GM 19422 and DMB 9101670 to Sidney Altman.

BACKGROUND OF THE INVENTION

This invention is in the general area of genetic engineering of nucleic acid sequences, especially RNA sequences that are substrates for Ribonuclease P.

There are several classes of ribozymes now known which are involved in the cleavage and/or ligation of RNA chains. A ribozyme is defined as an enzyme which is made of RNA, most of which work on RNA substrates. Ribozymes have been known since 1982, when Kruger, Kelly, et. al., "Self-Splicing RNA: Autoexcision and Autocyclization of the Ribosomal RNA Intervening Sequence of Tetrahymena," *Cell* 31:147-157 (1982) showed that a ribosomal RNA precursor in Tetrahymena, a unicellular eukaryote, undergoes cleavage catalyzed by elements in the RNA sequence to be removed during the conversion of the rRNA precursor into mature rRNA. Another class of ribozyme, discovered in 1983, was the first to be shown to work in trans (i.e., to work under conditions where the ribozyme is built into one RNA chain while the substrate to be cleaved is a second, separate RNA chain). This ribozyme, called M1 RNA, was characterized in 1983 by Altman and colleagues as responsible for the cleavage which forms mature 5' ends of all transfer RNAs (tRNAs) in *E. coli*. Analogous RNA-containing enzymes concerned with tRNA synthesis have since been found in all cells in which they have been sought, including a number of human cell lines, though the relevant eukaryotic RNAs have not yet been shown to be catalytic by themselves in vitro.

The discovery and characterization of this catalytic RNA is reviewed by Sidney Altman, in "Ribonuclease P: An Enzyme with a Catalytic RNA Subunit" in *Adv. Enzymol.* 62, 1-36 (1989). The activity was first isolated from *E. coli* extracts, and subsequently determined to be a ribonucleoprotein having two components, an RNA component called M1 and a protein component called C5. The RNA cleaved substrates in a true enzymatic reaction, as measured using Michaelis-Menton kinetics. M1 was determined to be solely responsible for substrate recognition and C5 was determined to alter $k_{cat}$ but not $K_M$, as reported by Guerrier-Takada, et al., *Cell* 35, 849 (1983) and McClain, et al., *Science* 238, 527 (1987). Sequencing showed that M1 RNA is 377 nucleotides long, $M_r$ approximately 125,000, and that the protein consists of 119 amino acids, $M_r$ approximately 13,800, as reported by Hansen, et al., *Gene* 38, 535 (1987).

Cleavage of precursor tRNA molecules by the RNA component of eubacterial RNAase P is described by Guerrier-Takada, et al., *Cell* 35, 849 (1983) and reviewed by Altman, *Adv. Enzymol.* 62, 1 (1989).

U.S. Pat. No. 5,168,053 entitled "Therapeutic Ribozyme Compositions" to Altman, et al., discloses that it is possible to target any RNA molecule for cleavage by bacterial RNAase P by forming a nucleotide sequence part of which is complementary to a targeted site and which includes a terminal 3'-NCCA, wherein the sequence is designed to hybridize to the targeted RNA so that the bacterial RNAase P cleaves the substrate at the hybrid base-paired region. Specificity is determined by the complementary sequence. The sequence is preferably ten to fifteen nucleotides in length and may contain non-complementary nucleotides to the extent this does not interfere with formation of several base pairs by the complementary sequence which is followed by NCCA at the 3' end.

Subsequent studies have demonstrated that the external guide sequence, or "EGS", that is useful in targeting procaryotic RNAase P, does not result in cleavage of a targeted RNA strand by eukaryotic RNAase P.

It is therefore an object of the present invention to provide methods and compositions for specifically cleaving targeted RNA sequences using eukaryotic RNAase P or functional equivalents thereof.

It is a further object of the present invention to provide methods and compositions for specifically cleaving RNA, both in vitro and in vivo within eukaryotic cells, for the treatment of disease conditions which involve RNA transcription or translation, such as diseases caused by RNA and DNA viruses and expression of excessive or pathogenic proteins from mRNA, or of excessive or pathogenic RNA, itself.

SUMMARY OF THE INVENTION

Any RNA can be targeted for cleavage by RNAase P from human cells, using a suitably designed oligoribonucleotide ("external guide sequence", or EGS) to form a hybrid with the target RNA, thereby creating a substrate targeted for cleavage by RNAase P in vitro. The data indicate that it is reasonable to conclude that these observations can be extended to RNAase P from any eucaryotic cell. The EGS contain a sequence which is complementary to the target RNA and which forms secondary and tertiary structure akin to portions of a tRNA molecule. The EGS must contain at least nucleotides which base pair with the target sequence 3' to the intended cleavage site to form a structure like the amino acyl acceptor stem, nucleotides which base pair to form a stem and loop structure similar to the T stem and loop, followed by one or two nucleotides that do not base pair to the target molecule followed by nucleotides that base pair with the target sequence to form a structure like the dihydrouracil stem. Methods are also disclosed to select EGS molecules having increased substrate affinity and utility in vivo to make a selected RNA a target for cleavage by the host cell RNAase P, thus preventing expression of the function of the target RNA. The methods and compositions should be useful to prevent the expression of disease-causing genes in vivo.

As described in the examples, parts of the EGS that participate in seconary and tertiary interactions were changed in the analogous tRNA structures in two ways. First, four nucleotides in the equivalent of the T loop and five in the equivalent of the variable loop were randomized by incorporation of equimolar quantities of the deoxynucleotides dA, dG, dC and T into a DNA template to yield an initial population of $2.6 \times 10^5$ sequence variants. Second, during each round of selective amplification, random mutations were introduced by performing PCR at an error rate of approximately 0.1 percent per nucleotide incorporated. A chimeric, covalently linked mRNA-EGS substrate was used to select sequences for the EGS that made it more efficient in guiding RNAase P to the target mRNA and selected for the ability of this substrate to be cleaved by human RNAase P. The chimeric RNA, with partially randomized sequence, was prepared by transcription in vitro of synthetic DNA templates. In each round of selection, the pool of RNAs was digested with human RNAase P and the cleaved products were isolated by electrophoresis and then amplified to produce progeny RNAs. The stringency of selection was increased at each cycle by reducing the amount of enzyme and the time allowed for the cleavage reaction, such that only those substrates that were cleaved rapidly by the enzyme were selected. Clones were then sequenced and, from the sequence that had been randomized in the T-loop, the sequences most frequently selected determined.

BRIEF DESCRIPTION OF THE DRAWINGS

In FIGS. 4A, 4B and 4C solid arrowheads denote the sites of cleavage by RNase T1, and arrows denote sites of cleavage by RNase T2. In FIGS. 4D, 4E and 4F, sites of cleavage by cobra venom nuclease are indicated by solid arrows.

FIG. 6A is an EGS (Sequence ID No. 36) forming an aminoacyl acceptor stem, T loop and stem, variable loop and stem, anticodon loop and stem, and D stem; FIG. 6B is an EGS (Sequence ID No. 37) wherein a G in the T loop is substituted for a C in the EGS of FIG. 6A; and FIG. 6C is an EGS (Sequence ID No. 38) where the anticodon loop and stem of the EGS of FIG. 6A is deleted.

DETAILED DESCRIPTION OF THE INVENTION

Figure 1:
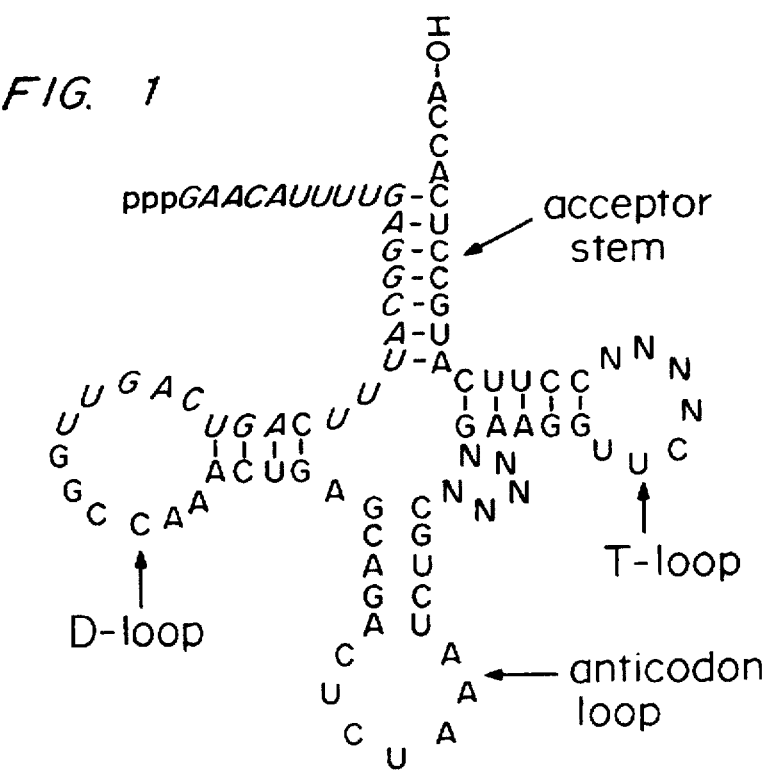
FIG. 1 is the proposed secondary structure of the chimeric substrate used in the selection procedure (Sequence ID No. 1). The italicized sequence is from CAT mRNA and the remaining sequence, aside from changes made to assure hydrogen bonding specifically to CAT mRNA, is based on the sequence of *E. coli* tRNA$^{Tyr}$. The nine nucleotides that were randomized are each indicated by N. Some of the EGS analogs for various parts of a tRNA are also depicted: acceptor stem, T loop, anticodon loop, and D-loop.

Ribonuclease P (RNAase P) from *E. coli* can cleave oligoribonucleotides that are found in hydrogen-bonded complexes that resemble the aminoacyl stem and include the 5' leader sequence of tRNA precursors, -NCAA. Human RNAase P cannot cleave in vitro the 5' proximal oligoribonucleotide in such simple complexes but can do so when the 3' proximal oligoribonucleotide is bound to an external guide sequence or EGS to form a structure resembling portions of a tRNA molecule. In a preferred embodiment, the EGS should include a complementary sequence to a target substrate of at least eleven nucleotides, seven bases which hydrogen bond to the targeted sequence to form a structure akin to the aminoacyl acceptor stem of a precursor tRNA, and four nucleotides which base pair with the targeted sequence to form a structure akin to the dihydrouridine stem. The EGS should also include sequence between the complementary sequence which forms a structure like the T stem and loop followed by at least one or two nucleotides which do not base pair with the target sequence or which form a variable loop.

The External Guide Sequence

A. RNAase P targeting Sequence.

An EGS for human RNAase P consists of a sequence which, when in a complex with the target substrate molecule, forms a secondary structure resembling that of a tRNA cloverleaf or a part of it. As used herein, the term "resembling a precursor tRNA" means a sufficient portion of the tRNA secondary structure to form a complex which will result in cleavage of the target RNA by RNAase P. The sequence of the EGS can be derived from any tRNA except that the D stem and aminoacyl stem have to be altered to be complementary to the target substrate sequence and the apparent D stem contains four base pairs. The presence of the 3'-CCA enhances the efficiency of the reaction with the human RNAase P by about 35%. The anticodon loop and stem and extra loop can separately be deleted and the T loop and stem can be modified without decreasing the usefulness of the EGS and, in the case of the anticodon stem and loop deletion, increases the efficiency of the reaction by about ten fold. Changes in other parts of an EGS can increase its efficiency about one hundred fold.

The desired secondary structure is determined using conventional Watson-Crick base pairing schemes to form a structure resembling a tRNA, i.e., having structure as described below. The specific sequence of the hydrogen bonded regions is not as critical, as long as the desired structure is formed. All tRNAs, including tRNAs from a wide variety of bacteria and eukaryotes, conform to the same general secondary structure. This is typically written in the form of a cloverleaf, maintained by hydrogen-bonded base pairing between short complementary regions. The four major arms are named for their structure or function: The acceptor arm consists of a 3' terminal $CCA_{OH}$ plus a variable fourth nucleotide extending beyond the stem formed by base-pairing the 5' and 3' segments of the molecule. The other arms consist of base-paired stems and unpaired loops. The "T" arm is named for the presence of the ribothymidine nucleotide and contains seven unpaired bases in the loop. The anticodon arm always contains the anticodon triplet in the center of the loop and consists of seven unpaired bases. The D arm is named for the presence of the base dihydrouridine in the loop, another of the modified bases in tRNA, and includes between eight and twelve unpaired bases. Positions are numbered from 5' to 3' according to the most common tRNA structure, which has 76 residues. The overall range of tRNA lengths is from 74 to 95 bases. The variation in length is caused by differences in the structure of two of the arms, the D arm and the extra or variable arm, which lies between the T and anticodon arms, which can contain between three and five bases, or between 13 and 21 bases with a stem of about five bases. The base pairing that maintains the secondary structure is virtually invariant: there are always seven base pairs in the acceptor stem, five in the T arm, five in the anticodon arm, and three or four in the D arm.

As used herein, a hybrid structure, consisting of an EGS hydrogen bonded to an RNA substrate, having secondary structure resembling a precursor tRNA under conditions promoting cleavage by RNAase P of the substrate at the nucleotide at the 5' end of the base-paired region, preferably includes a D stem, an aminoacyl stem, a variable loop of at least one or two nucleotides, and a T loop and stem, where the latter may be modified compared to the sequence and detailed structure found in the parent molecule.

A few nucleotides are always found in the same positions in 90 to 95% of tRNAs, with some additional nucleotides being semiconserved (or semivariant). This is not a requirement in the EGS, as long as the sequence is complementary to the target and forms the secondary structure characteristic of the tRNA. In fact, the sequence forming the aminoacyl stem and D loop and stem are changed in the EGS to be complementary to the target RNA.

The base paired double-helical stems of the secondary structure are maintained in the tertiary structure, creating two double helices at right angles to each other. The acceptor stem and the T stem form one continuous double helix with a single gap; the D stem and the anticodon stem form another continuous double helix, also with a gap. Many of the invariant and semi-invariant bases are involved in the tertiary structure.

B. Method for Producing EGSs having enhanced efficacy.

Methods for selection of modified EGSs having enhanced binding affinity as measured by decreased energy of binding were designed by modifying protocols for evolution in vitro reported by Tuerk and Gold, *Science*, 249:505 (1990); Green et al., *Nature*, 347: 406 (1990); Chowrira et al., *Nature*, 354:320 (1991); Berzal-Heranz et al., *Genes and Dev.*, 6:129 (1992); and Beaudry and Joyce, *Science*, 257: 635- (1992). These methods were used to identify RNA molecules with desired properties from pools of molecules that contain randomized sequences. As demonstrated more clearly in the examples, appropriately modified, these methods can be used for the isolation of efficient EGSs. These new EGSs, when complexed with CAT mRNA substrate (Sequence ID No. 7), allow cleavage of the target by human RNAase P at rates similar to those achieved with natural substrate.

Figure 2:
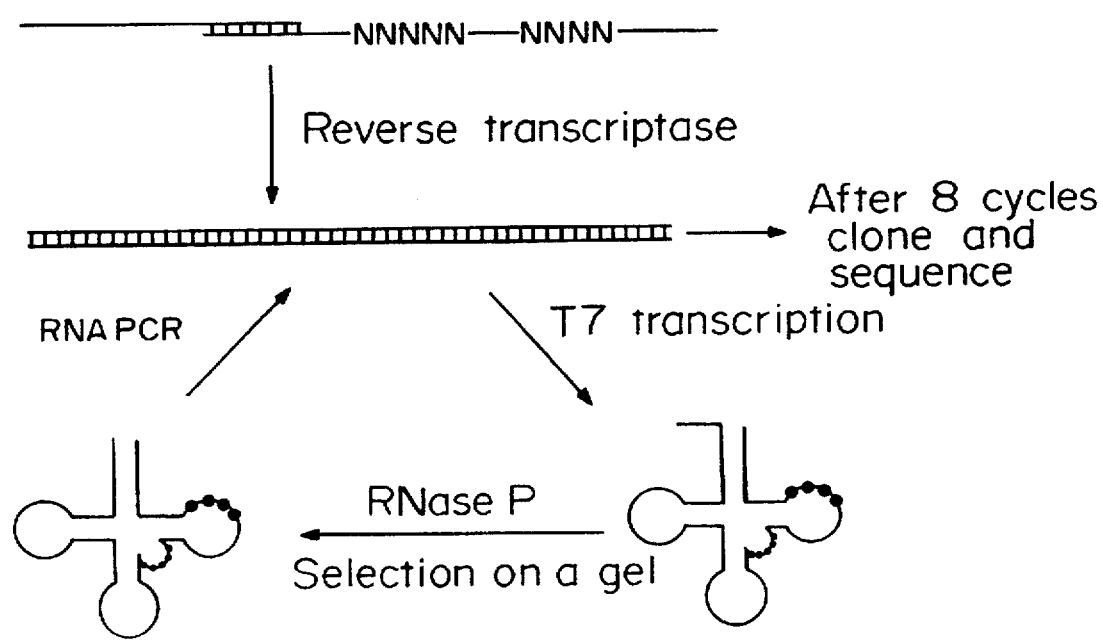
FIG. 2 depicts the general scheme for in vitro selection and amplification of chimeric substrates with enhanced efficiency for directing human RNAase P cleavage. "Reverse transcriptase" denotes that the DNA polymerase capability of reverse transcriptase was used to create double-stranded template DNA from the overlapping DNA oligonucleotides SEC-1A (Sequence ID No. 2) and SEC-1B (Sequence ID No. 3). "RNA-PCR" refers to reverse transcription coupled to PCR.

The general selection scheme is depicted in FIG. 2. In each round of selection, the pool of RNAs is digested with human RNAase P and the cleaved products are isolated by electrophoresis and then amplified to produce progeny RNAs. One of the template-creating oligonucleotides is used as the 5' primer for the polymerase chain reaction (PCR) in order to allow restoration of the promoter sequence and the leader sequence of the chimeric RNA for the next cycle of selection. The stringency of selection is increased at each cycle by reducing the amount of enzyme and the time allowed for the cleavage reaction, such that only those substrates that are cleaved rapidly by the enzyme are selected.

In the first three rounds of selection, RNA substrates are digested with 3.6 units of human RNAase P. One unit of human RNAase P is defined as that amount of enzyme that cleaves 1 pmol of precursor to $tRNA^{Tyr}$ from *E. coli* in 30 min at 37° C. For assays in subsequent rounds of selection, the amount of enzyme is reduced, and the incubation time is shortened so that less than 20 percent of the substrate is cleaved. Cleavage products are separated from uncleaved substrates by electrophoresis and RNA extracted.

The purified cleavage product RNAs are reverse transcribed and amplified by PCR. The double-stranded DNA generated by PCR regains the promoter sequence and the leader sequence from the sequence in the primer, and is then used as a template for transcription of RNA for the next round of selection. After eight cycles of selection, the resulting pool of double-stranded DNAs is cloned into an appropriate vector and sequenced.

In order to test the abilities of EGSs derived from the individual variants, sequences corresponding to the EGS segment of each chimeric tRNA are amplified by PCR, and RNAs transcribed with an appropriate RNA polymerase. EGS-directed RNA cleavage is then assayed. Sequences in common in the most active EGS are then determined and new EGS designed.

As described in the examples, simulation of evolution in vitro was used to select EGSs that bind strongly to a target substrate mRNA and that increase the efficiency of cleavage of the target by human ribonuclease P to a level equal to that achieved with natural substrates. The most efficient EGSs from tRNA precursor-like structures with the target RNA, in which the analog of the anticodon stem has been disrupted, an indication that selection for the optimal substrate for ribonuclease P yields an RNA structure different from that of present-day tRNA precursors.

C. Complementary Sequence.

The complementary sequences will generally consist of eleven nucleotides in two blocks which base pair with the target sequence, and which are separated by two unpaired nucleotides in the target sequence, preferably UU, wherein the two blocks are complementary to a sequence 3' to the site targeted for cleavage.

Ribonuclease P.

Ribonuclease P (RNAase P) is an enzyme consisting of protein and RNA subunits that cleaves tRNA precursors to generate the 5' termini of tRNAs. This essential enzymatic activity has been found in all cell types examined, both prokaryotic and eukaryotic. During the studies on recognition of substrate by RNAase P, it was found that *E. coli*

RNAase P can cleave synthetic tRNA-related substrates that lack specific domains (the D, T and anticodon stems and loops) of the normal tRNA structure. A half-turn of an RNA helix and a 3' proximal CCA sequence contain sufficient recognition elements to allow the reaction to proceed. The 5' proximal sequence of the RNA helix does not have to be covalently linked to 3' proximal sequence of the helix. The 3' proximal sequence of the stem can be regarded as an "external guide sequence" (EGS) because it identifies the site of cleavage in the 5' proximal region through a base-paired region.

RNAase P from *E. coli* and human cells have similar but not identical biochemical properties. Their RNA components have similar secondary structures. However, the substrate range of human RNAase P is much narrower than that of the *E. coli* enzyme. For example, although *E. coli* RNAase P can cleave a synthetic tRNA-related substrate that lacks three specific domains (the D, variable, and anticodon stem and loop) of the normal tRNA structure, the human enzyme and the structurally similar enzyme from the yeast, *S. cerevisiae*, cannot cleave the same substrate. However, the *E. coli* RNAase P can cleave a synthetic tRNA-related substrate that is also cleaved by the human RNAase P.

As used herein, unless otherwise specified, RNAase P refers to the RNAase P in the cell in which the RNA to be cleaved is located, whether endogenous, added to the cell, or as used in vitro. Many of the techniques described herein are known to those skilled in the art, as are methods for making, and sources of, reagents. The teachings of any references cited herein with respect to methods and reagents are specifically incorporated herein, as well as for the purpose of demonstrating the scope and level of skill in the art.

It is not necessary to provide RNAase P activity if the cleavage is to occur intracellularly in the nucleus since all cells contain RNAase P in their nuclei. RNAase P must be supplied if cleavage is to occur in the cytoplasm. As used herein for ease of convenience, RNAase P refers to the ribonucleoprotein consisting of the eukaryotic analogues of the *E. coli* C5 protein and M1 RNA, regardless of source, whether isolated, produced by chemical synthesis or, in the case of the RNA, transcription from the gene, referred to herein as H1 RNA. The RNA subunit need not necessarily manifest catalytic activity in the absence of protein subunits in vitro.

A. Endogenous RNAase P.

The sequence and proposed secondary structure of H1 RNA, the RNA component of human RNAase P, was reported by Baer, et al., in *Nucleic Acids Res.* 18(1), 97–103 (1989), the teachings of which are incorporated herein. The sequence of H1 DNA is included as Sequence ID No. 11.

Because of the similarity in secondary structure and substrate specificity among the RNAase P's of diverse origin, it is possible to use an EGS designed to maximize efficiency of cleavage for the RNAase P in question using techniques described herein to target any RNA in any cell, even though the catalytically active RNA subunits may have distinctly different sequences. See Altman, *Ann. Rev. Enzymology* 62, 1–39(1989); Altman, *J. Biol. Chem.* 265, 20053–20056 (1990). Secondary structure is defined by intramolecular associations of complementary sequences. Base pairs can be canonical, A/U and G/C, or non-canonical, G/U, A/G, etc.

B. Exogenous RNA having catalytic activity.

An EGS can also be used in combination with an RNA sequence that demonstrates enzymatic activity in the presence or absence of a protein. That RNA sequence can be represented by a molecule like the entire H1 RNA molecule or any portion thereof shown to have catalytic activity in combination with a protein, or any functionally equivalent molecule of eukaryotic origin or derivation. As noted above, an EGS effective to convert a targeted sequence into a substrate for human RNAase P, will also be effective in making substrate a target for procaryotic RNAase P.

There are two principle situations in which catalytic exogenous RNA or RNAase P is utilized in combination with EGS: in vitro in the absence of cells or cellular RNAase P and in circumstances wherein the RNA to be cleaved is located in a portion of a cell not containing endogenous RNAase P. In the latter case, the genes encoding the analogs of M1 RNA and C5 protein (as defined above), or the human or other eucaryotic equivalents thereof, are introduced into the cell at the desired location for cleavage using a suitable vector or other method known to those skilled in the art for introduction and expression of a gene in a cell.

Application of the EGS as laboratory or clinical reagents.

The external guide sequences have applications as in vitro reagents, in a similar fashion to restriction enzymes, and as therapeutic agents, for cleavage and inactivation of specific host cell RNA or RNA coded for by pathogenic organisms such as bacteria or viruses, as demonstrated by the following examples.

As used herein, the EGS is referred to as an RNA molecule. It is to be understood, however, that for therapeutic purposes, a DNA molecule encoding the EGS molecule could be utilized. Accordingly, unless otherwise specified, the term "EGS" encompasses both the RNA molecule that hydrogen bonds to a target nucleic acid sequence that is cleaved by RNAase P, as well as a DNA molecule encoding the RNA molecule, which is expressed under conditions wherein the RNA molecule functions as an EGS.

The external guide sequence, including the combination of eleven bases complementary to a sequence on the 3' side of the desired cleavage site and specific to the targeted RNA and a portion forming the T stem and loop and a portion of the variable loop, can be added to any RNA having sequences complementary to the EGS, in the presence of RNAase P, and the RNA will be cleaved at the targeted site. In this manner, the activity of endogenous RNAase P in any cell, such as the RNAase P of human cells, can be directed to destroy specific messenger, viral or other RNAs by the use of an appropriate EGS RNA.

1. Reagents for in vitro applications.

DNA restriction endonucleases are invaluable reagents for the molecular biologist. Patterns of restriction fragment sizes are used to establish sequence relationships between DNA molecules, and large DNAs can be cleaved to give fragments of sizes useful for genetic engineering, sequencing, and studying protein binding. RNA processing enzymes can be utilized under conditions such that they also cleave RNA with considerable sequence specificity.

Specific ribozymes can be prepared by combining the specific guide sequence with eukaryotic RNAase P or functional equivalents thereof. In the preferred embodiment, the external guide sequence and the RNA subunit of RNAase P (e.g., H1 RNA) are separate; alternatively, the two sequences can be combined using an oligonucleotide linker that allows sufficient flexibility between the targeting sequence and the H1 RNA (or equivalent) sequence for the targeting guide sequence to bind and the catalytic sequence, whether in association with an analog of C5 protein or not, to cleave.

2. Therapeutics.

a. Determination and Preparation of Complementary Sequences.

Any cellular gene product expressed as RNA, including proteins encoded by mRNA and structural RNAs themselves, can be targeted for inactivation by RNAase P using sequences engineered to include appropriate regions of sequence and/or structure for binding to the targeted RNA and the desired site of cleavage. The cellular gene product could be a modified product of an oncogene, such as the ras gene product; where the product is not a normal cell component, a viral protein, such as one encoded by an essential gene for HIV replication; or a bacterial protein.

In many cases, the critical genes in an infective or pathological agent have been isolated and sequenced. Appropriate complementary sequences can be synthesized using standard techniques, reagents, and equipment based on these known sequences.

b. Preparation of an appropriate pharmaceutical composition for delivery of the EGS to the targeted RNA.

There are two primary mechanisms for delivering the EGS to intracellular RNA that has been targeted for cleavage: diffusion and via a vector.

As discussed above, any RNA that is important in a disease process can be targeted and appropriate complementary sequences made synthetically or by copying cloned sequence. Since RNAase P is predominantly found in the nucleus of eukaryotic cells, the infectious agents most likely to be inhibited by administration of appropriate EGS to the infected cells are those in which critical RNA sequences are transcribed in the nucleus. Important examples of the viral agents that replicate in the cell nucleus include herpes viruses (including herpes simplex virus, varicella-herpes zoster virus, cytomegalovirus, and Epstein-Barr virus), hepatitis B virus, adenoviruses, paramyxoviruses such as measles, and the retroviruses, such as human immunodeficiency virus (HIV I, HIV II, HIV III and HTLV-1).

Vector-mediated delivery of EGS.

Preferred vectors are viral vectors such as the retroviruses which introduce the EGS directly into the nucleus where it is transcribed and released into the nucleus. Under the appropriate conditions, the EGS will hybridize to the targeted RNA and the endogenous RNAase P will cleave the hybridized RNA at the 5' side of the hybrid region.

Methods for using retroviral vectors for gene therapy are described in U.S. Pat. Nos. 4,868,116 and 4,980,286, and PCT application PCT/US89/03794 and PCT/US89/00422, the teachings of which are incorporated herein.

Defective retroviral vectors, which incorporate their own RNA sequence in the form of DNA into the host chromosome, can be engineered to incorporate the EGS into the host, where copies will be made and released into the cytoplasm to interact with the target nucleotide sequences.

The ability to introduce specifically engineered nucleic acid sequences, as a means of targeted therapy, into hematopoietic cells of patients suffering from virus-induced disease of those cells, such as AIDS, has great potential. The most efficacious methodology presently available for the introduction of specific genetic sequences into human cells involves the use of RNA-containing retroviruses which serve as vehicles or vectors for high efficiency gene transfer into human cells.

RNAase P-based therapy can also be used as a means of preventing the spread of HIV-1 and or providing a HIV-1 resistant population of T-cells that will be able to confer immune function to infected individuals. Patients who have been recently diagnosed as having antibodies to HIV-1, but who do not yet show AIDS symptomatology, are the most likely be the best candidates for therapy. This procedure will necessitate removal of some of the patient's bone marrow stem cells and subsequent partial cytoblation. The removed cells can be treated in the laboratory with appropriate EGS compositions (via appropriate viral vectors, such as defective viral vectors) and then restored to the same individual. The treated cells will develop in the patient into mature hematopoietic cells, including T-cells. These T-cells will have normal immune function and, most importantly, will be intracellularly immunized to prevent their destruction by any HIV-1 still present in the patient.

Bone marrow stem cells and hematopoietic cells are relatively easily removed and replaced and provide a self-regenerating population of cells for the propagation of transferred genes. As described above, HIV-1 and HTLV-1 should be amenable to these approaches. In the longer term, it is anticipated that the use of RNAase P-based therapeutics will allow the selective inactivation of other unwanted genes in cells, such as activated oncogenes, involved in the causation and maintenance of cancer cells.

In contrast to the approaches presently in use which are aimed at preventing or limiting infection with HIV, it should be possible to use RNAase P-based technology to treat, and possibly to cure, HIV infection, and related diseases of white blood cells which are subject to transformation by retroviral vectors carrying EGS. Particular examples of diseases that may be treated using EGS to target RNA for cleavage by RNAase P include not only HTLV-1, but also various retroviral-induced leukemias resulting from chromosomal translocations that produce chimeric RNAs which produce proteins that are unique to those cells and that can act as growth stimulators or oncogenes. Other types of transformed tissues that might be treatable include all cancer cells carrying identified oncogenes of known sequence.

Topical and other EGS compositions for local administration.

The EGS may also be administered topically, locally or systemically in a suitable pharmaceutical carrier. *Remington's Pharmaceutical Sciences*, 15th Edition by E. W. Martin (Mark Publishing Company, 1975), the teachings of which are incorporated herein by reference, discloses typical carriers and methods of preparation. The EGS may also be encapsulated in suitable biocompatible microcapsules, microparticles or microspheres formed of biodegradable or non-biodegradable polymers or proteins or liposomes for targeting to phagocytic cells. Such systems are well known to those skilled in the art and may be optimized for use with the appropriate EGS sequences.

Therapeutically the oligoribonucleotides are administered as a pharmaceutical composition consisting of an effective amount of the EGS to inhibit transcription of a targeted RNA and a pharmaceutically acceptable carrier. Examples of typical pharmaceutical carriers, used alone or in combination, include one or more solid, semi-solid, or liquid diluents, fillers and formulation adjuvants which are non-toxic, inert and pharmaceutically acceptable. Such pharmaceutical compositions are preferable in dosage unit form, i.e., physically discreet units containing a predetermined amount of the drug corresponding to a fraction or multiple of the dose which is calculated to produce the desired therapeutic response. It is essential that the oligonucleotides be delivered in a form which prevents degradation of all of the oligonucleotide before it reaches the intended target site.

A preferred composition is a topical composition, for example, for application to a viral lesion such as that produced by herpes simplex virus. These will generally contain between 1 µM and 1 mM oligonucleotide/unit of carrier, or produce a concentration between 1 µM and 1 mM at the site of the cells to be treated. Oral compositions, although not preferred, are in the form of tablets or capsules and may contain conventional excipients. Another preferred composition is a polymeric material applied locally for release of EGS. Still another preferred composition is a solution or suspension of the EGS in an appropriate vector in combination with conventional pharmaceutical vehicles are employed for parenteral compositions, such as an aqueous solution for intravenous injection or an oily suspension for intramuscular injection.

For clinical applications, the dosage and the dosage regimen in each case should be carefully adjusted, utilizing sound professional judgment and consideration of the age, weight and condition of the recipient, the route of administration and the nature and gravity of the illness.

The present invention, a RNA sequence targeting a second RNA sequence for cleavage by eukaryotic RNAase P, will be further understood by reference to the following non-limiting examples.

Example 1

Cleavage of tRNA precursor fragments by human RNase P in the presence of EGS.

Figure 3A:
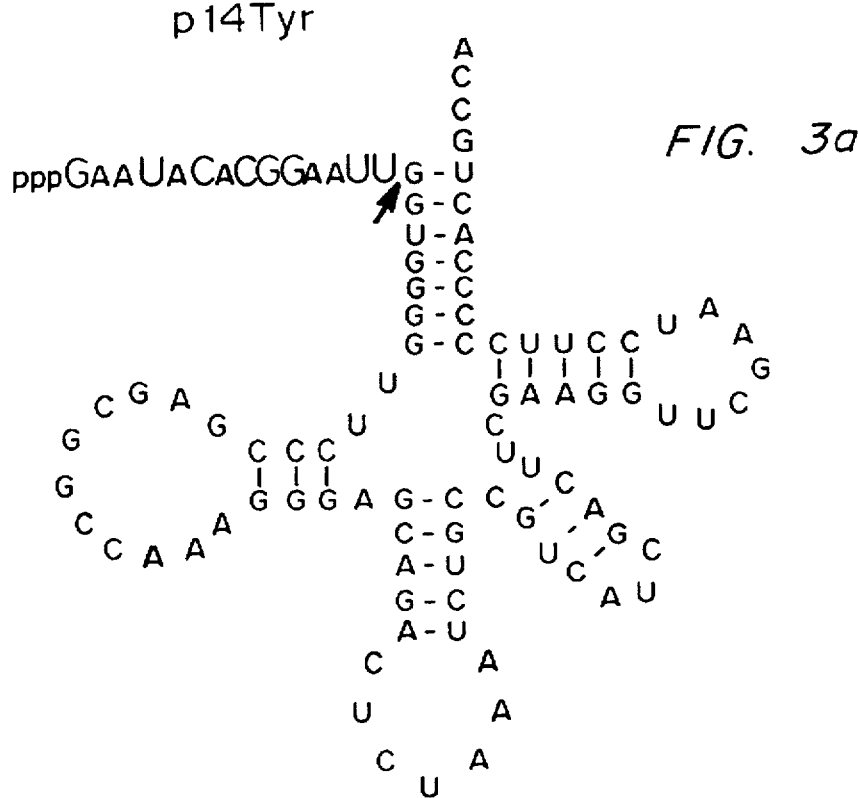
FIG. 3 is the sequence and secondary structures of the precursor to tRNA$^{Tyr}$ (Sequence ID No. 4) and a complex of a substrate and EGS▲(1–18) (Sequence ID No. 5), which is derived from tRNA$^{Tyr}$ but lacks the first eighteen nucleotides from the 5' end of the mature tRNA$^{Tyr}$. pTyr: *E. coli* tRNA$^{Tyr}$ precursor; pAva: substrate (target) RNA with 5' leader sequence and the first fourteen nucleotides of *E. coli* tRNA$^{Tyr}$ (Sequence ID No. 6).
Figure 3B:
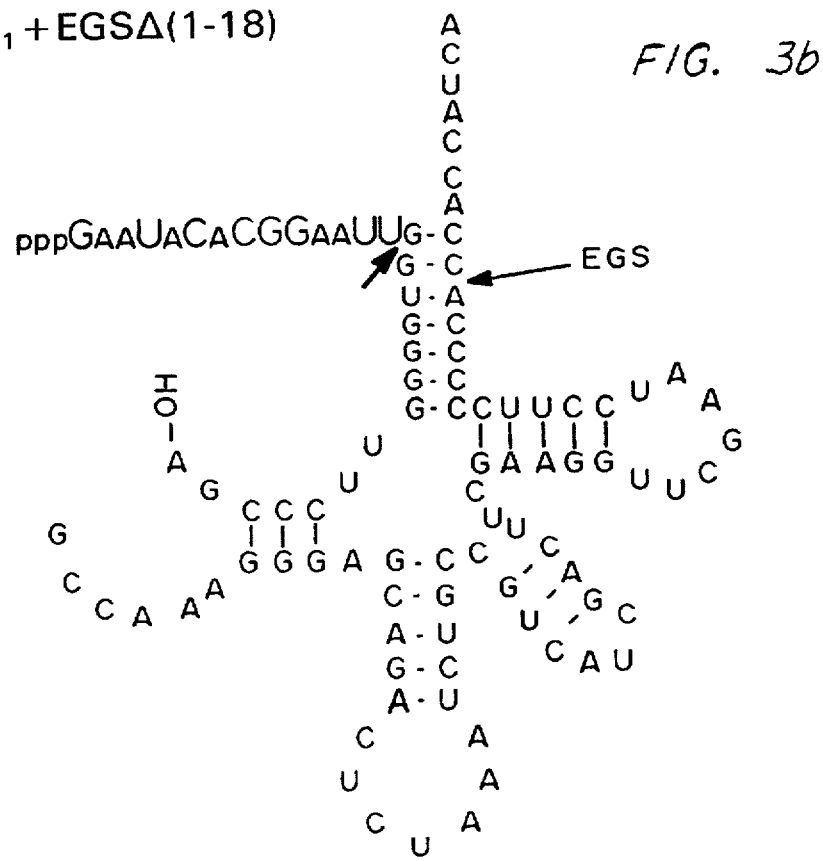

An EGS that can target RNA for cleavage by human RNase P was prepared using a small RNA fragment, pAva (Sequence ID No. 6, FIG. 3) which contains a 5' precursor sequence and the first fourteen nucleotides from the 5' terminus of a tRNA. The leader sequence of $E.\ coli$ tRNA$^{Tyr}$ precursor can be cleaved correctly when another piece of RNA, i.e., EGS▲1–18 (Sequence ID Nos. 5), which lacks the first eighteen nucleotides of the 5' terminus of mature tRNA$^{Tyr}$ but retains the remaining 3' proximal sequence, is hybridized to the target RNA.

Human RNAase P was partially purified from HeLa cells using the method of Bartkiewicz et al. $Genes\ and\ Development$ 3:488–499 (1989). The substrates were prepared by in vitro transcription in the presence of [$\alpha$-$^{32}$P]GTP. [$\alpha$-$^{32}$P] GTP labelled pAva (Sequence ID No. 6) I RNA (28 nt) was mixed with unlabelled EGS RNA and the mixture was incubated at 37° C. in 50 mM Tris-Cl (pH 7.5), 100 mM NH$_4$Cl, and 10 mM MgCl$_2$ with enzyme for 30 min. Labelled pAva(Sequence ID No. 6) I RNA alone was also incubated with or without enzyme. Analysis by gel electrophoresis shows that the EGS plus enzyme resulted in cleavage of the RNA.

The 3' proximal oligonucleotide is the external guide sequence (EGS). Because the lengths of the leaders and their sequences, as well as the sequences of the mature domain, are not conserved among different precursor-tRNAs, the main determinants for human RNAase P cleavage must be in some of the conserved structural features of various tRNAs. This general idea is borne out by the fact that several other EGSs that did not mimic exactly the structure of parts of a tRNA (i.e., changes in the number of possible base pairs in the D or amino acyl stems, changes in positions 8 and 9 of the mature tRNA sequence, and a change from cytosine to uracil at position 57) did not target complementary RNAs. However, an EGS that lacked the anticodon stem and loop, or the variable stem and loop, resulted in efficient cleavage, indicating that these parts of the EGS, separately, were not essential for recognition of the target complex by the enzyme.

Accordingly, if an mRNA, rather than part of a precursor tRNA sequence, is incorporated into the double-stranded stem region of a putative target complex, and the resulting hybrid contains the structural features required of a substrate for human RNAase P activity, the mRNA should be cleaved by human RNAase P.

Example 2

Specific cleavage of CAT mRNA in vitro by human RNAase P using an external guide sequence.

Examples provided below show the efficiency of cleavage of the mRNA for chloramphenicol acetyltransferase (CAT) by human RNAase P. The sequence of the 5' oligoribonucleotide, as well as that of the EGS, depends on the choice of target site in the mRNA. The presence of the appropriately designed EGS efficiently reduces CAT enzymatic activity in vivo, as well as promotes cleavage of CAT mRNA in vitro, indicating that this method should be of general use for gene inactivation.

Figure 4A:
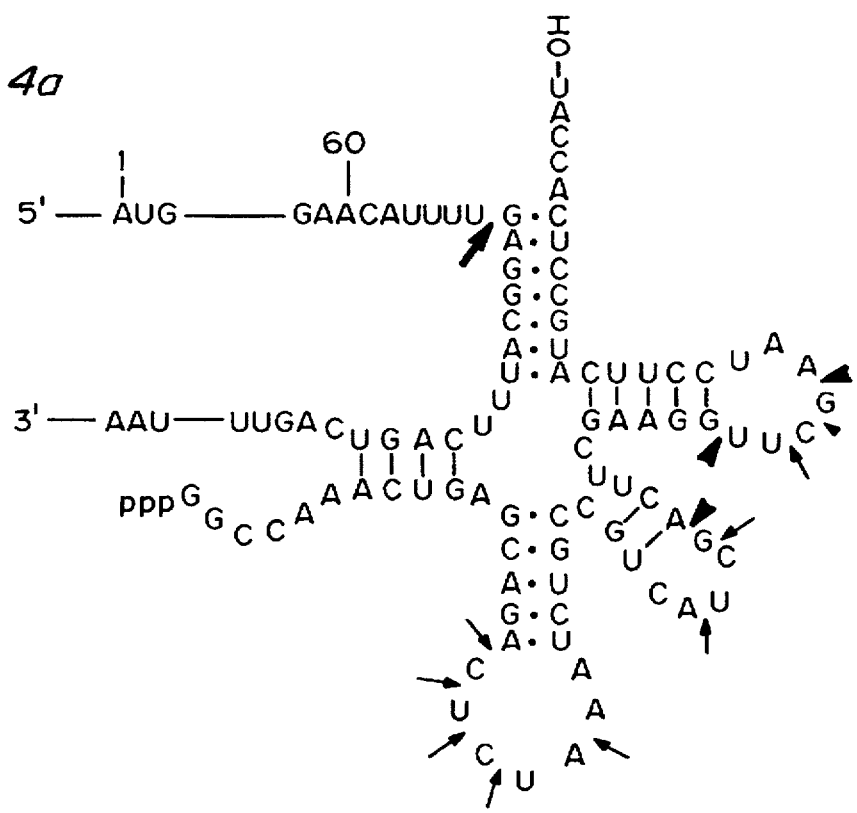
FIGS. 4A, 4B, 4C, 4D, 4E, and 4F are the proposed secondary structures of complexes of CAT mRNA and various EGS. 4A and 4D depict complexes between the complementary region CAT mRNA (Sequence ID No. 7) and EGS$^{CAT}$ (Sequence ID No. 8). 4B and 4E are complexes of CAT mRNA (Sequence ID No. 7) and EGS 9 (Sequence ID No. 9). 4C and 4F are complexes of CAT mRNA (Sequence ID No. 7) and EGS$^{CAT}$▲AC (Sequence ID No. 10). Hollow arrows denote sites of cleavage by human RNAase P.

An EGS custom-designed for the mRNA for chloramphenicol transacetylase (CAT), shown in FIG. 4A, EGS$^{CAT}$, Sequence ID No. 8), can direct the specific cleavage of CAT mRNA by human RNAase P in vitro or in vivo cells in tissue culture. However, the cleavage reaction is inefficient compared to cleavage of natural tRNA precursor substrates.

The proposed secondary structure of a complex of CAT mRNA (Sequence ID No. 7) and EGS$^{CAT}$ (Sequence ID No. 8) resembles the tRNA cloverleaf structure, but it includes sequences not normally found in the tRNA from which it was originally derived (tyrosyl tRNA (tRNA$^{Tyr}$) (Sequence ID No. 6) of $Escherichia\ coli$). To ensure that appropriate tertiary interactions that facilitate the process of enzyme-substrate recognition exist in the complex, parts of the EGS that participate in tertiary interactions in the analogous tRNA structures were changed in two ways. First, four nucleotides in the equivalent of the T loop and five in the equivalent of the variable loop were randomized by incorporation of equimolar quantities of the deoxynucleotides dA, dG, dC and T into a DNA template to yield an initial population of 2.6×10$^5$ sequence variants. Second, during each round of selective amplification, random mutations were introduced by performing polymerase chain reaction (PCR) at an error rate of approximately 0.1 percent per nucleotide incorporated, using the method of A. Beaudry and G. F. Joyce, $Science$ 257:635 (1992)). The mRNA for the gene for chloramphenicol acetyltransferase (CAT) can be easily manipulated on plasmids and the enzymatic activity is readily expressed in tissue culture cells so it was used as a target substrate. As demonstrated below, an EGS can target CAT mRNA (Sequence ID No. 7) for specific cleavage by human RNAase P. FIG. 4A shows a complex in which an EGS, EGS$^{CAT}$ (Sequence ID No. 8), could base-pair with nucleotides 67 to 79 (where the first nucleotide of the translation initiation codon is numbered 1) of CAT mRNA (Sequence Listing ID No. 7) and direct human RNAase P to cleave that mRNA at nucleotide 67. The EGS$^{CAT}$ (Sequence ID No. 8) construct was derived from the $E.\ coli$ tRNA$^{Tyr}$ (Sequence ID No. 6) gene where the first eighteen nucleotides from the 5' terminus have been deleted and the sequences on the D-loop and acceptor-loop have been changed to make base-pairs with CAT mRNA. The EGS$^{CAT}$ (Sequence ID No. 8) fused upstream with a T7 promoter was cloned into a pUC19 vector. The EGS$^{CAT}$ RNA (Sequence ID No. 8) was prepared through in vitro transcription with T7 RNA polymerase. A HindIII-BamHI DNA fragment of the CAT gene (pCAT™, Promega) was cloned in pGem-2. The CAT DNA was linearized with EcoRI and transcribed with T7 RNA polymerase in the presence of [$\alpha$-$^{32}$P]GTP. Labeled CAT mRNA was mixed with various amounts of the EGS$^{CAT}$ (Sequence ID No. 8) molecule without special treatment of denaturing or annealing and susceptibility to cleavage by RNAase P in vitro was tested with human RNAase P partially purified from HeLa cells.

The HindIII - BamHI fragment of CAT gene (pCAT™, Promega) was cloned in pGem-2. The plasmid was truncated with EcoRI and a 260 nucleotide-long transcript was obtained by in vitro transcription with T7 RNA polymerase in the presence of [α-$^{32}$P]GTP. The EGS sequence was synthesized by polymerase chain reaction, using the E. coli tRNA$^{Tyr}$ gene as template, with oligonucleotide GCCAAACTGAGCAGACTC (Sequence Listing ID No. 12) and GCGCggtaccAAAAATGGTGAGGCATGAAGG (Sequence Listing ID No. 13), where the bold letters in the oligonucleotide sequences indicate the bases needed to make base pairs to CAT mRNA, the underlined letters indicate the sequence complementary to the transcription termination signal, and the lower case letters shows an extra linker sequence (GCGC at the 5' end of the second oligonucleotide are extra nucleotides). The PCR fragment was digested with Hind III and cloned into pUC19 with a T7 promoter upstream from the EGS sequence. The EGS$^{CAT}$ RNA (Sequence ID No. 8) was transcribed with T7 RNA polymerase after the plasmid was linearized with DraI. A mixture of unlabelled and [α-$^{32}$P]GTP labelled CAT mRNA fragment (0.2 pmole in total) was mixed with the EGS$^{CAT}$ RNA (Sequence ID No. 8) in amount of 4 pmole, 1 pmole, 1 pmole, 0.4 pmole and 0.2 pmole. Each mixture was incubated at 37° C. in 50 mMTris-Cl (pH 7.5), 100 mM NH$_4$Cl, and 25 mM MgCl$_2$ with enzyme for one hour. The reaction was stopped by addition of an equal volume of dye solution with excess EDTA and then subjected to a 5% polyacrylamide-7M urea gel. CAT mRNA alone was incubated without and with enzyme and loaded on the gel.

Primer extension analysis determining the precise site of EGS$^{CAT}$-directed cleavage by human RNAase P was conducted as follows. A reverse transcription reaction was performed on the uncleaved and cleaved CAT mRNA using an oligodeoxyribonucleotide GGCCGTAATATCCAGCTGAACGG (Sequence Listing ID No. 14), complementary to nucleotides 129 to 107 of CAT mRNA. The reaction was incubated in 100 mMTris-Cl (pH 8.3), 10 mM KCl, 6 mM MgCl$_2$, 10 mM DTT and 2 units AMV reverse transcriptase at 46° C. for 2 hours. Labelled G, A, U, C were used as reference analyses of DNA sequences corresponding to the CAT mRNA template.

The precise site of cleavage of CAT mRNA was determined by primer extension analysis using an oligodeoxyribonucleotide primer complementary to nucleotide 129–107 of the RNA shows that the cleavage occurs between nucleotides 66 and 67, as expected.

The results of the EGS$^{CAT}$ RNA-directed cleavage of CAT mRNA were analyzed by gel electrophoresis. In the presence of EGS$^{CAT}$ (Sequence ID No. 8) molecules, CAT mRNAs were cleaved to give rise to two products with the expected size. Analysis of the products of the reaction showed that the end groups contained 5' phosphoryl and 3' hydroxyl termini, the same as those normally generated by RNAase P. The results show conclusively that the specific cleavage of CAT mRNA is due to an EGS-directed RNAase P hydrolytic reaction.

For up to five-fold molar excess of EGS$^{CAT}$ RNA to mRNA, the cleavage efficiency is proportional to the amount of EGS$^{CAT}$ added. However, more than ten-fold excess of EGS$^{CAT}$ molecules caused a decrease in the cleavage efficiency. One explanation for this is that EGS$^{CAT}$ alone inhibits the enzymatic activity by competing with the mRNA-EGS complex for the enzyme. The reaction proceeds in a linear fashion for more than 3 hours at 37° C. Denaturation and reannealing of the oligonucleotides in the target complex did not improve the efficiency of cleavage. The reaction has an absolute requirement for Mg$^{2+}$ with an optimal concentration of 25 mM, in contrast to that with tRNA$^{Tyr}$ precursor as substrate, which has an optimal Mg$^{2+}$ concentration of between 2 and 10 mM.

Example 3

Inhibition of Expression of CAT activity in green monkey CV-1 cells by EGS$^{CAT}$.

In order to test whether the EGS can function in vivo, the EGS$^{CAT}$ sequence (Sequence ID No. 8) was inserted downstream of a mouse U6 snRNA gene promoter in a BLUESCRIPT™ (Stratagene, La Jolla, Calif.) vector forming pEGS$^{CAT}$. The EGS$^{CAT}$ sequence (Sequence ID No. 8) can be transcribed by RNA polymerass III and the transcription can terminate at a T$_5$ cluster following the EGS sequence in either S100 extract or living cells. Green monkey fibroblast cells CV-1 were cotransfected with pCAT and pEGS$^{CAT}$ plasmids. After transfection with pCAT, which encodes the CAT gene, and pEGS$^{CAT}$, cells were harvested and CAT activity was assayed.

CV-1 cells were maintained in Dulbecco's modified Eagle medium that contained 10% fetal calf serum. One day prior to transfection cells were split 1:10 and plated in 60 mm Petri plates. Two hours prior to transfection cells were fed with 4.5 ml of fresh medium with 10% fetal calf serum. Transfection was performed using the calcium phosphate precipitation procedure using 2.5 μg of pCAT DNA and various amounts of pEGS$^{CAT}$ DNA, ranging from one to 6.25 μg. Twenty-four hours after transfection, cells were harvested and cell extracts were assay for CAT activity.

The extract from cells cotransfected with EGS$^{CAT}$ construct apparently decreased the conversion of chloramphenicol to its acetylated forms. The degree of inhibition was measured quantitatively by counting of the spots excised from a TLC plate. EGS$^{CAT}$ cotransfection produced greater than 50% inhibition compared to the control with no EGS$^{CAT}$ cotransfection. There was substantial loss of ability to inhibit CAT expression when a higher ratio of pEGS$^{CAT}$ to pCAT was introduced. Similar experiments yielding approximately 70% of CAT activity have also been performed with human cells in tissue culture.

Example 4

Preparation of Modified EGS enhancing degradation of target RNA by RNAase P.

As explained in detail below, two classes of EGS were designed, as shown in FIGS. 4A, 4B, 4C, 4D, 4E, and 4F (the EGS in 4A and 4D, 4B and 4E, and 4C and 4F are the same). The first class involves deletions of large segments of the EGS as suggested in Example 1 and described in Examples 2 and 3. For example, it has been found that the anticodon loop and stem can be deleted, as shown in EGS$_{CAT}$▲AC (Sequence ID No. 10) of FIG. 4C and 4F, and the EGS can still promote cleavage by RNAase P of a target RNA (CAT mRNA containing Sequence ID No. 7 in FIGS. 4C and 4F). The anticodon loop and part of the variable loop can alternatively be deleted from the EGS, and the EGS will promote cleavage with greater efficiency than the parent EGS molecule. The most efficient EGS of this deletion class was the one in which the anticodon stem and loop was deleted. This EGS$^{CAT}$▲AC (Sequence ID No. 10) promoted cleavage by human RNAase P of a target mRNA (CAT mRNA) at a rate 10-fold higher than the parent EGS. The deletion of both variable and anticodon stems and loops, however, does not yield a more efficient EGS, although the variable loop can consist of only one or two nucleotides and still be highly efficient.

The second class of EGSs have changes in both the equivalent of the T loop, the variable loop, and the anticodon stem of the tRNA-like segment of the EGS. Three such EGSs, described below, are EGS 6, EGS 8 and EGS 9 (Sequence ID No. 9, FIGS. 4B and 4E). As shown below, EGS 9 is the most efficient of the EGSs in these examples and directs cleavage by human RNAase P of a target RNA (CAT mRNA) at a rate approximately fifty to one hundred fold greater than the parent EGS.

These results apply to relative rates of cleavage at a particular site in a target mRNA. The absolute rates of cleavage at any particular site still depend on access of the EGS to that particular site.

Example 5

Preparation of RNAs with randomized nucleotides.

Preparation of Chimetic Covalently Linked mRNA-EGS Substrate.

The procedure to select for EGSs that are more efficient in guiding RNAase P to the target CAT mRNA involves the synthesis of a population of chimeric, covalently linked mRNA-EGS substrates which are then run through cycles of in vitro mutation and selection for molecules which can serve as substrates for RNAase P. Double-stranded DNA templates were made by annealing of and enzymatically extending two overlapping synthetic oligonucleotides: TAATACGACTCACTATAGAA-CATTTTGAGGCATTTCAGTCAGTT GGCCAAACTGAGCAGAC (SEC-1A, Sequence ID No. 2) and TGGTGAGGCATGAAGGNNNNGAACCT-TCNNNNNGCAGATTTAGAGTCTGCTCAGTTTGGCC (SEC-1B, Sequence ID No. 3), where the complementary sequences are underlined and the randomized nucleotides (N) were introduced during their machine synthesis by incorporating equimolar quantities of four nucleotides. These sequences create a chimeric tRNA gene which contains sequences from CAT mRNA and tRNA$^{Tyr}$ from *E. coli* as well as nine nucleotides (N) that are randomized. A promoter for T7 bacteriophage RNA polymerase is included in SEC-1A (Sequence ID No. 2). The extension was carried out with AMV reverse transcriptass at 46° C. for two hours. Variant RNA pools were prepared by transcription with T7 polymerase in 40 mM Tris. Cl. pH 7.9, 6 mM MgCl$_2$ 10 mM dithiothreitol 2 mM spermidine 1 mM NTPs containing 20 µCi [α-$^{32}$P]GTP at 37° C.

The selection procedure.

The general selection scheme is described above. One of the template-creating oligonucleotides (SEC-1A, Sequence ID No. 2) was also used as the 5' primer for the polymerase chain reaction (PCR) in order to allow restoration of the T7 promoter sequence and the leader sequence of the chimeric RNA for the next cycle of selection. The stringency of selection was increased at each cycle by reducing the amount of enzyme and the time allowed for the cleavage reaction, such that only those substrates that were cleaved rapidly by the enzyme were selected.

In the first three rounds of selection, RNA substrates were digested with 3.6 units of human RNAase P, purified through the glycerol gradient step described by Yuan and Altman, *Proc. Natl. Acad. Sci. USA*, 89: 8006–8010 (1992) and Bartkiewicz et al., *Genes and Dev.*, 3, 488 (1989)) in 50 mMTris-Cl (pH 7.5), 10 mM MgCl$_2$, and 100 mM NH$_4$Cl at 37° C. for 2 hours. One unit of human RNAase P is defined as that amount of enzyme that cleaves 1 pmol of precursor to tRNA$^{Tyr}$ from *E. coli* in 30 min at 37° C. For assays in subsequent rounds of selection, the amount of enzyme was reduced, and the incubation time was shortened so that less than 20 percent of the substrate was cleaved.

Cleavage products were separated from uncleaved substrates by electrophoresis on an eight percent polyacrylamide-7M urea gel. RNA was extracted from the gels by the crush and soak method.

The purified cleavage product RNAs were reverse transcribed and amplified by PCR with SEC-1A (Sequence ID No. 2) and SEC-1C (TGGTGAGGCATGAAGG, Sequence ID No. 15) as primers with a Perkin Elmer RNA PCR kit. The double-stranded DNA generated by PCR regained the T7 promoter sequence and the leader sequence from the sequence in the primer SEC-1A, and it was then used as a template for transcription of RNA for the next round of selection.

Characterization of the selected RNAs and EGS RNA derived from them.

After eight cycles of selection and the resulting pool of double-stranded DNAs were cloned into the BLUE-SCRIPT™ vector (Stratagene, La Jolla, Calif.) vector. Eighteen plasmid DNAs were sequenced using Sequenase 2.0 (U.S. Biochemicals, Cleveland, Ohio).

In order to test the abilities of EGSs derived from the individual variants selected above for CAT mRNA targeting, sequences corresponding to the EGS segment of each chimeric tRNA were amplified by PCR using primers SEC-1A (Sequence ID No. 2) and SEC-1T (TAATACGACTCACTATAGGCCAACTGAGCAGAC, Sequence ID No. 16), which contains a promoter sequence for T7 polymerase, and RNAs were transcribed with T7 RNA polymerase. EGS-directed CAT mRNA cleavage was assayed in 10 µl of 50 mMTris-Cl, pH 7.5, 10 mM MgCl$_2$ 100 mM NH$_4$Cl containing 0.25 pmol (1000 cpm) of substrate RNA and 1 or 5 pmol of EGS RNAs. Reaction mixtures were incubated at 37° C. for 30 min with 10 units of RNAase P from HeLa cells, followed by electrophoresis in 5% polyacrylamide/7M urea gels.

The gels showed a species of RNA migrating in the position expected for cleavage of substrate RNA in those lanes where the newly selected EGSs have been included in the reaction mixtures.

Sequence Analysis of Randomized EGSs.

Sixteen individual clones were sequenced. The sequence of the anticodon stem/loop, the variable (V) loop, and the T stem/loop are shown in FIG. 6. From the sequence that had been randomized in the T-loop, two particular sequences were most frequently selected: UUCGUGC (seven clones) and UUCGCCC (seven clones). The T loop sequences of the two remaining clones contained single transition mutations of the two major sequences (UUCG<u>U</u>CC and UUC<u>A</u>CCC). By contrast, no significant sequence-related bias was seen in the sequence of five nucleotides in the variable loop.

In addition to the sequences in the T and variable loops that were selected from the totally randomized sequence, a considerable number of mutations were introduced into the EGS in the chimeric substrates as a consequence of the conditions for PCR. Some of these mutations were beneficial and, therefore, the sequences that included them were selected and accumulated. In almost all of the individual selected clones, the integrity of base-pairing in the anticodon stem was disrupted.

Table 1 shows the partial sequences of the anticodon loop/stem region, the variable (V) loop, and the T stem/loop region of the parent chimeric mRNA-EGS$^{CAT}$ substrate (P, Nucleotides 28 through 88 of Sequence ID No. 1) and of the EGS segments of some individual chimeric mRNA-EGS substrates (nucleotides 1 through 60 of Sequence ID No. 9 and Sequence ID Nos. 17 through 31) which were obtained as a result of the in vitro selection procedure. Nucleotides that differ from the parent chimeric mRNA-EGS$^{CAT}$ substrate sequence are given in bold letters and are underlined. Hyphens indicate deletions. The remaining part of the sequence of the mRNA-EGS chimeric substrates is shown in FIG. 4A. Numbering of the partial sequences is not uniformly consecutive, since some clones did not have appropriate inserts and only sixteen selected sequences are listed.

The most dramatic improvement in rates occurred with the EGS sequence based on clone 9 (EGS 9, nucleotides 1 through 60 of Sequence ID No. 9), which directed cleavage of the CAT mRNA at an overall rate more than 30 times faster than that observed with EGS$^{CAT}$ in the complex. The three most efficient EGSs tested, derived from clone 6, clone 8 and clone 9, all had a common sequence, UUCGUGC, in the T loop.

Secondary structural analysis of mRNA-EGS complexes.

The proposed secondary structure of the complex of CAT mRNA and EGS 9 (Sequence ID No. 9) (FIG. 4B) can be compared with the parent CAT mRNA-EGS$^{CAT}$ complex (FIG. 4A). The structures of CAT mRNA-EGS complexes were confirmed in part by partial digestion with RNases T1 and T2 under conditions that allowed formation of the mRNA-EGS complex and identification of single-stranded regions in RNA. Partial digestion of CAT mRNA-EGS complexes with RNases T1 and T2 (Pharmacia) were performed in RNAase P assay buffer (50 mM Tris-HCl (pH

TABLE 1

| Substrate # (ID No. Sequence) | D stem/ loop | Anticodon stem/loop | V loop | T stem/ loop | AA stem |
|---|---|---|---|---|---|
| | 19 | 30 | 47 | 52 | 69 |
| SCE-1 (28–88 of 1) | GGCCAAACUGA | GCAGACUCUAAAUCUGC | NNNNN | GAAGGUUCNNNNCCUUC | AUGCCUCACCA |
| #1 (17) | GGCCAAACUGA | GCAGACUCUAAAUC<u>G</u>GC | <u>CCUUC</u> | GAAGGUUC<u>G</u>CCCCUUC | AUGCCUCACCA |
| #2 (18) | GGCCAAACUGA | GCAGACUCUAAAUCUGC | <u>ACGAGA</u> | GAAGGUUC<u>GUG</u>CCCUUC | AUGCCUCACCA |
| #4 (19) | GGCCAAACUGA | GCAGACUCUAAA<u>C</u>UGGC | <u>CUAAC</u> | GAAGGUUC<u>G</u>CCCCUUC | AUGCCUCACCA |
| #5 (20) | GGCCAAACUGA | GCAGACUCUAAAU-UGC | <u>CCAAC</u> | GAAGGUUC<u>ACC</u>CCUUC | AUGCCUCACCA |
| #6 (21) | GGCCAAACUGA | GCAGACUC<u>C</u>AAAUC–C | <u>ACCAA</u> | GAAGGUUC<u>GUG</u>CCCUUC | AUGCCUCACCA |
| #8 (22) | GGCCAAACUGA | GCAGACUCUAAA-CU<u>C</u>C | <u>UCCCA</u> | GAAGGUUC<u>GUG</u>CCCUUC | AUGCCUCACCA |
| #9 (1–60 of 9) | GGCCAAACUGA | GCAGACUCUAAAUC-GC | <u>AAACG</u> | GAAGGUUC<u>GUG</u>CCCUUC | AUGCCUCACCA |
| #10 (23) | GGCCAAACUGA | GCAGACUCUAAAUC<u>G</u>GC | <u>CUACG</u> | GAAGGUUC<u>G</u>CCCCUUC | AUGCCUCACCA |
| #11 (24) | GGCCAAACUGA | GCAGAC<u>G</u>CUAAAUC<u>U</u>AC | <u>CCCGU</u> | GAAGGUUC<u>GUC</u>CCCUUC | AUGCCUCACCA |
| #12 (25) | GGCCAAACUGA | GCAGACUCUAAAU<u>U</u>UGC | <u>CACCA</u> | GAAGGUUC<u>G</u>CCCCUUC | AUGCCUCACCA |
| #13 (26) | GGCCAAACUGA | GCAGACUC-AAAUCUGGC | <u>CAUUC</u> | GAAGGUUC<u>G</u>CCCCUUC | AUGCCUCACCA |
| #14 (27) | GGCCAAACUGA | GCAGACUCUAAAUC-GC | <u>AGUGU</u> | GAAGGUUC<u>GUG</u>CCCUUC | AUGCCUCACCA |
| #15 (28) | GGCCAAACUGA | GCAGACUCUAAAUC<u>A</u>GC | <u>GCGUG</u> | GAAGGUUC<u>GUG</u>CCCUUC | AUGCCUCACCA |
| #16 (29) | GGCCAAACUGA | GCAGACUCUAAAUC<u>G</u>GC | <u>CGCAC</u> | GAAGGUUC<u>G</u>CCCCUUC | AUGCCUCACCA |
| #17 (30) | GGCCAAACUGA | GCAGAC<u>A</u>CUAAAU<u>U</u>UGC | <u>ACGAG</u> | GAAGGUUC<u>G</u>CCCCUUC | AUGCCUCACCA |
| #18 (31) | GGCCAAACUGA | GCAGAC<u>CC</u>UAAAUCUGC | <u>CCCCG</u> | GAAGGUUC<u>GUG</u>CCCUUC | AUGCCUCACCA |

Synthesis and analysis of individual EGS RNAs based on selected chimeric substrates.

The best chimeric substrate selected was clone 9 whose corresponding RNA sequence is partially shown in sequence 9 (nucleotides 1 through 60 of Sequence ID 9) in Table 1. The clone 9 chimeric substrate was cleaved about 5.5 times more efficiently than the parent, non-randomized, chimeric substrate, mRNA-EGS$^{CAT}$ chimera. Using the sequences of the selected chimeric substrates, nine individual corresponding EGS RNAs were synthesized: EGS-1 (Sequence ID No. 17), EGS-4 (Sequence ID No. 19), EGS-5 (Sequence ID No. 20), EGS-6 (Sequence ID No. 21), EGS-8 (Sequence ID No. 22), EGS-9 (nucleotides 1 through 60 of Sequence ID No. 9), EGS-12 (Sequence ID No. 25), EGS-14 (Sequence ID No. 27) and EGS-18 (Sequence ID No. 31), in order to probe the function of these selected EGSs in directing RNAase P to the target CAT mRNA.

Each of the individual EGS RNAs was mixed with $^{32}$P-labeled CAT mRNA and the mixtures were then exposed to RNAase P. Every selected EGS RNA increased the initial rate of the cleavage reaction, as measured during the linear phase of the reaction, over that with EGS$^{CAT}$, and cleavage occurred at the expected site in the target mRNA, as demonstrated by FIG. 5.

7.5), 10 mM MgCl$_2$, and 100 mM NH$_4$Cl). The reaction mixture contained substrate RNA labeled with [$^{32}$p] at its 5' terminus (2000 cpm), 0.2 mg/ml of rat 5S RNA as carrier, and three different concentrations, 2×10$^{-4}$, 1×10$^{-3}$ and 5×10$^{-3}$ units/ml, of RNase T1 or RNase T2. Reactions were incubated at room temperature for 5 min. The samples were analyzed by PAGE in 12.5% sequencing gels. Double-stranded regions were identified by digestion with cobra venom nuclease (Pharmacia, Alameda, Calif.). Conditions for digestion with cobra venom nuclease were as described above for RNase T1 and T2 except that incubation was at 37° C.

Figure 4B:
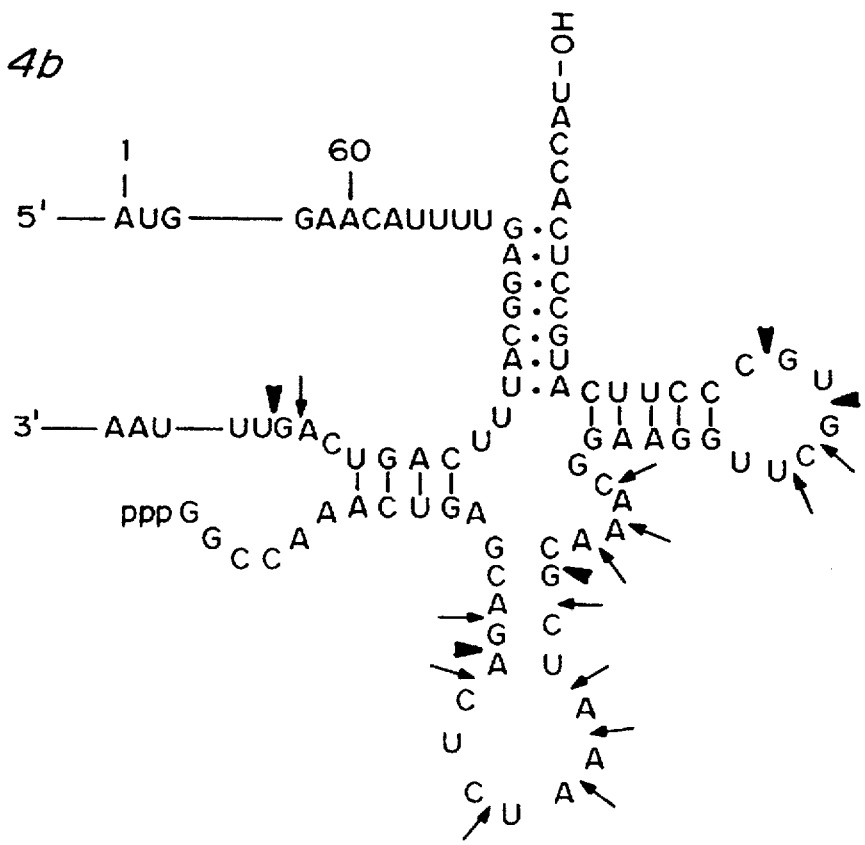
Figure 4C:
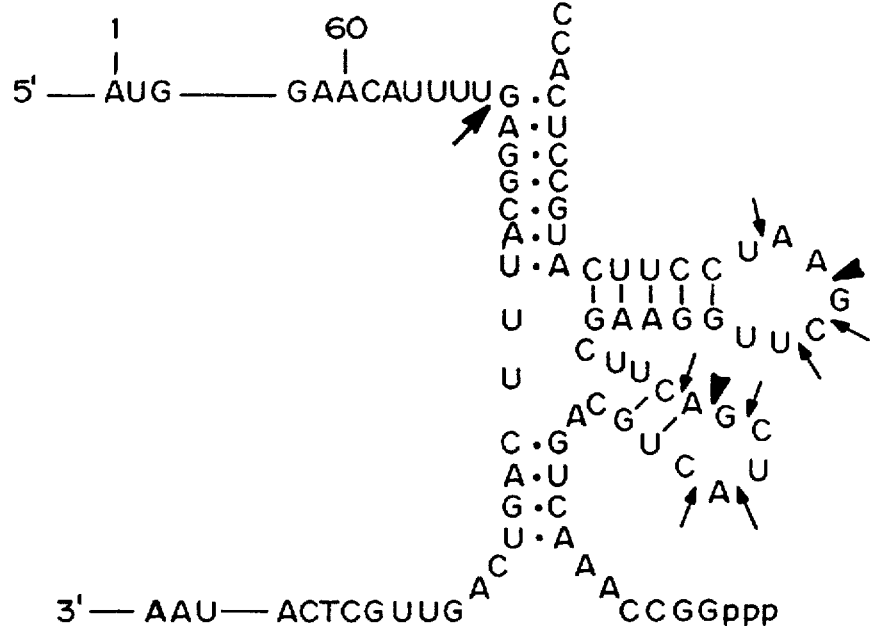
Figure 4D:
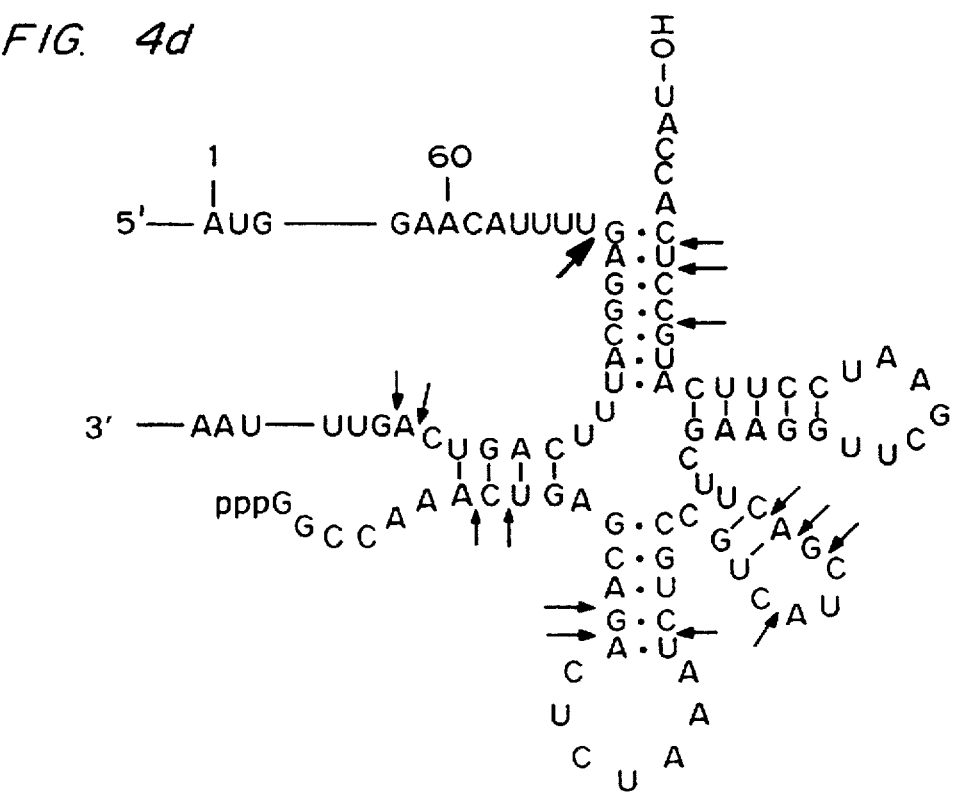
Figure 4E:
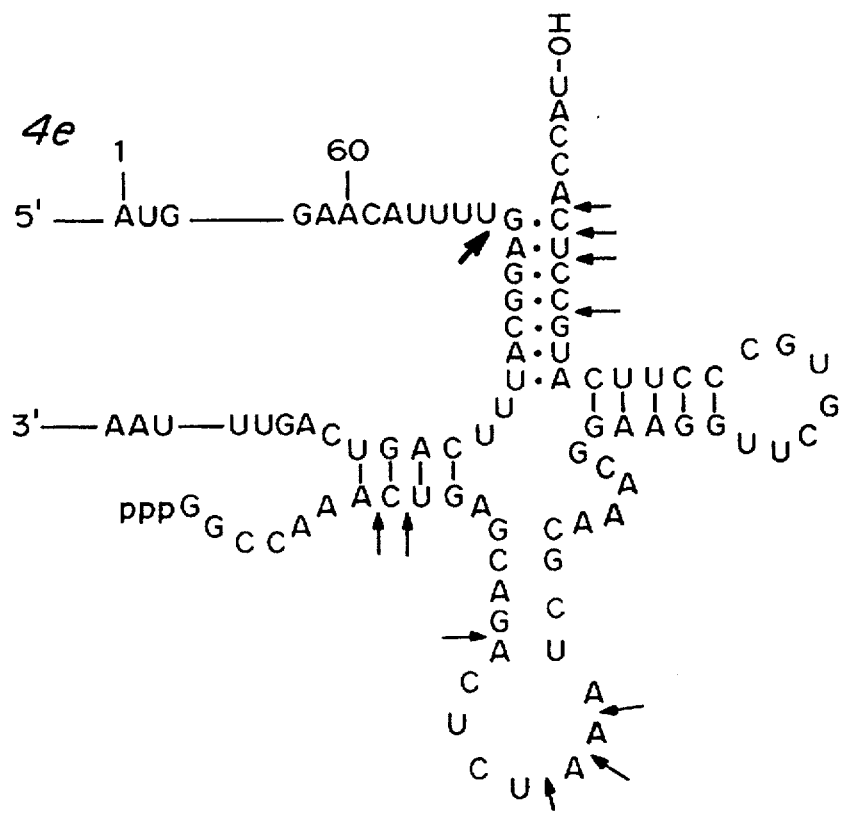
Figure 4F:
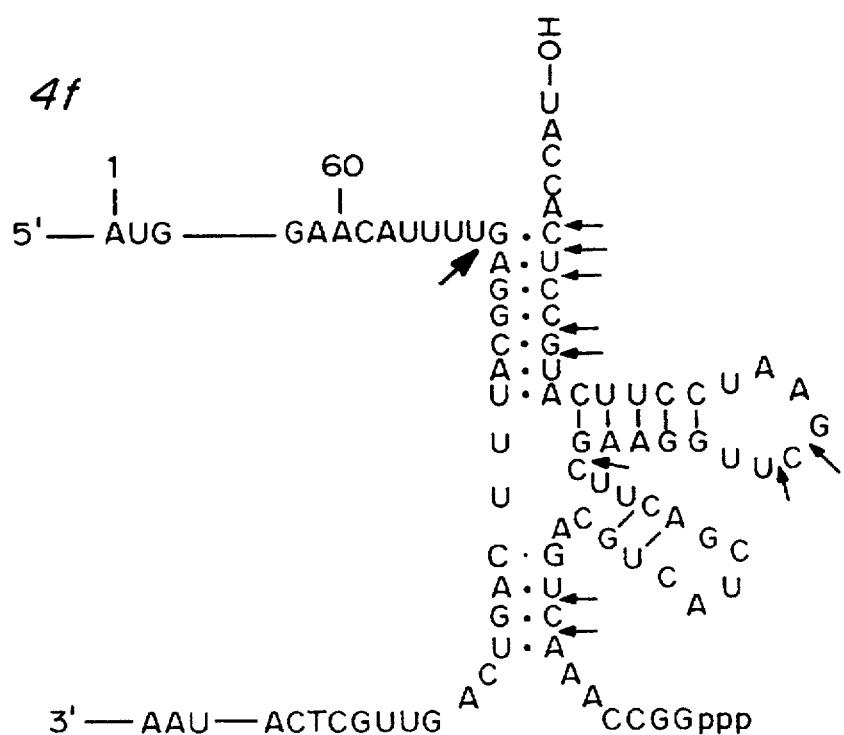

The sites of cleavage by the various nucleases in CAT mRNA-EGS$^{CAT}$ complex are indicated by solid arrows in FIGS. 4A and 4D. The tRNA domain in this structure is very similar to that found in a natural tRNA. The results obtained with cobra venom nuclease indicate that the first few nucleotides in the analog of the D loop are involved in a tertiary interaction, presumably with nucleotides in the variable loop (FIG. 4D). This interaction is either absent or much less extensive in the complex with EGS 9 (Sequence ID No. 9) (FIG. 4E) and, indeed, the same region in the analog of the D loop is susceptible to attack by RNases T1 and T2, an indication that it is in a single-stranded conformation (FIG.

4B). This result, together with the appearance of new sites of susceptibility to attack by cobra venom in the anticodon loop of EGS 9 confirm that this EGS endows the complex of the EGS and CAT mRNA with new tertiary interactions that enhance the rate of cleavage by RNAase P. The results of cleavages by nucleases also confirmed that the anticodon stem in EGS 9 was disrupted as a result of a single nucleotide deletion. EGSs 9 and 14 are not similar to each other in terms of their efficiency in directing RNAase P to a target substrate. The only difference in their nucleotide sequences is in the variable loop, as shown by Table 1. This difference alone must account for the relative inefficiency of EGS 14 in terms of targeting ability. Furthermore, digestion with RNase T1 of the complex that contained EGS 9 revealed strong protection of the last nucleotide, G, in the variable loop from attack by RNase T1, as shown by FIG. 4B. The role of this G may be similar to that played by nucleotide 57 in tertiary interactions in tRNA molecules; namely, the G may form hydrogen bonds with a nucleotide in the CAT mRNA sequence to ensure folding of the "tRNA" domain of the mRNA sequence.

Anticodon stem and loop of an EGS decrease cleavage rate of RNAase P and are dispensable.

An independent study of recognition of precursor tRNA substrates by human RNAase P showed that the anticodon stem and loop form a dispensable structural feature in the recognition of substrates by human RNAase P. To determine whether the anticodon stem and loop may act in a negative fashion on the overall rate of cleavage of target RNA by RNAase P, two more EGS RNAs were constructed, one being a deletion mutant that lacked the equivalent of the anticodon stem and loop, $EGS^{CAT}\blacktriangle AC$ (Sequence ID No. 10), as compared to the parent $EGS^{CAT}$ (FIG. 4A), and the other, EGS 19, being a derivative of EGS 9 in which the structure of the anticodon stem was restored.

DNA coding for $EGS^{CAT}\blacktriangle AC$ was synthesized by PCR with $pEGS^{CAT}$ DNA (Yuan et al., Proc. Nat. Acad. Sci. USA, 89, 8006 (1992)) as template; and oligonucleotide EC-1▲AC (GCCAAACTGACGTCATCGACTTCG, Sequence ID No. 32) and M13 reverse primer (AACAGCTATGACCATG, Sequence ID No. 33) were used as primers. The DNA generated by PCR was digested with HindIII and then inserted into pUC19 downstream from a T7 RNA polymerase promoter sequence. $EGS^{CAT}\triangle AC$ RNA (Sequence ID No. 10) was prepared by transcription in vitro after the new plasmid DNA had been linearized with DraI. DNA that coded for EGS 19 was synthesized by PCR procedure in a manner similar to that used for the synthesis of DNA for EGS 9, with oligonucleotides SEC-1C (Sequence ID No. 15) and SEC-1I (GTAATACGACTC-ACTATAGGCCAAACTGAGCAGACTCTAAATC TGCAAACGGA AGGTTC, Sequence ID No. 34): the newly inserted T residue in SEC-1I is underlined. The DNA was transcribed in vitro with T7 RNA polymerase to give EGS 19 RNA. EGS 19 (Sequence ID No. 39) RNA differs from EGS 9 RNA only in the additional U that restores the structure of the anticodon stem.

Figure 5:
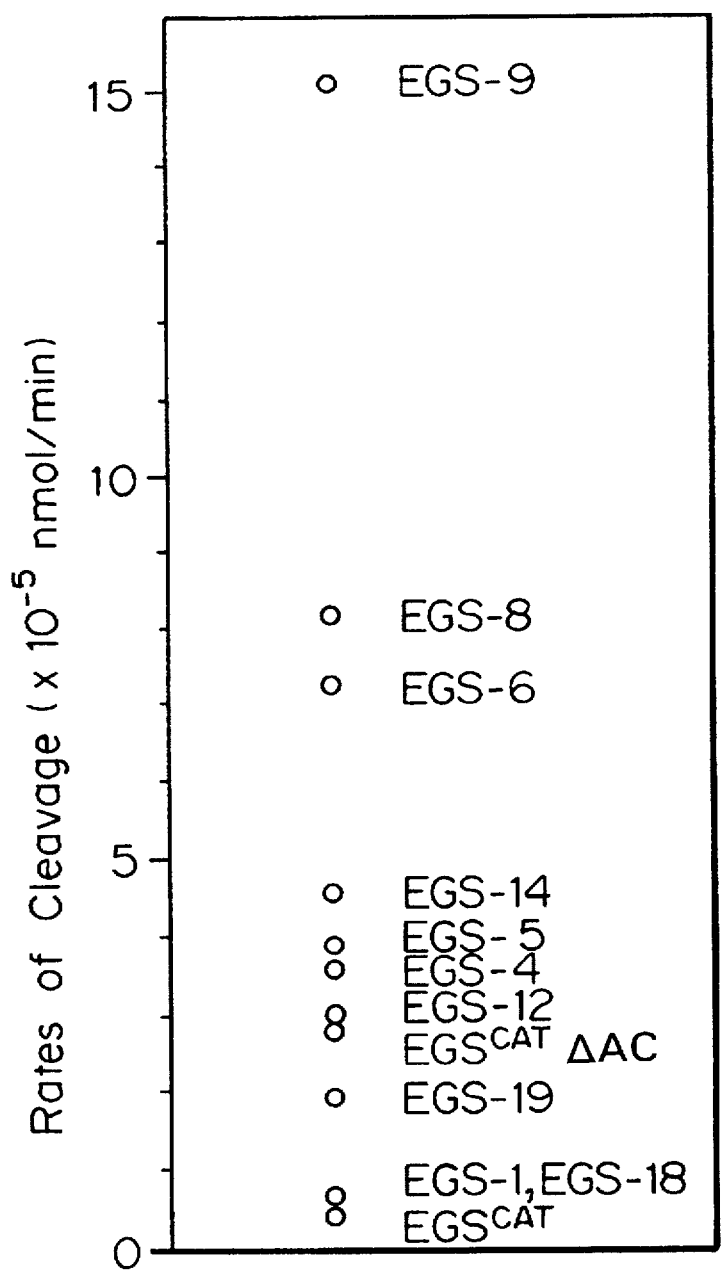
FIG. 5 shows rates (nmol/min) of human RNAase P cleavage of CAT mRNA directed by twelve individual EGS RNAs. Nine individual EGS RNAs: EGS 1 (Sequence ID No. 17), EGS 4 (Sequence ID No. 19), EGS 5 (Sequence ID No. 20), EGS 6 (Sequence ID No. 21), EGS 8 (Sequence ID No. 22), EGS 9 (Sequence ID No. 9), EGS 12 (Sequence ID No. 26), EGS 14 (Sequence ID No. 27), EGS 18 (Sequence ID No. 31), were prepared by in vitro selection. EGS 19 and EGS$^{CAT}$▲AC (Sequence ID No. 10) were prepared by in vitro mutagenesis. Results are presented as initial rates (nmol/mol) of cleavage of substrate by RNAase P during the linear phase of each reaction.

In $EGS^{CAT}\triangle 1387AC$ (Sequence ID No. 10), the length of $EGS^{CAT}$ was reduced by 25%: the shorter deletion mutant directed cleavage of target RNA about six times more efficiently than the parent EGS, as shown by FIG. 5. Restoration of the anticodon-stem structure, as in EGS 19, reduced the rate of cleavage of the target RNA with EGS 19 to four times lower than that with EGS 9. These results, together with the measurement of the rates of reaction with EGSs selected in vitro, indicate a significant inverse correlation between the efficiency of an EGS in the cleavage reaction and the existence of an anticodon stem in EGS RNA.

Stability of EGS-mRNA complexes.

The stability of EGS-mRNA complexes was measured based on both the binding constants between the mRNA and each EGS and the dependence on $Mg^{2+}$ ions of the cleavage reaction (presuming that relatively high concentrations of $Mg^{2+}$ ions were needed to stabilize relatively unstable complexes). The dissociation constants ($K_d$) of mRNA-EGS complexes were measured directly by a gel mobility shift assay in polyacrylamide gels that contained 10 mM $Mg^{2+}$ ions according to the method of Pyle et al., Proc. Natl. Acad. Sci. USA, 87: 8187–8191 (1990)). A fragment of CAT mRNA, 160 nucleotides in length, was prepared by transcription with T7 RNA polymerase in the presence of $[\alpha-^{32}P]GTP$. EGS RNA (10 μl) in 2X binding buffer was heated at 80° C. for 4 min before it was mixed with an equal volume of 2 nM CAT mRNA fragment in water (1X binding buffer contains 50 mM Tris-Cl (pH 7.5), 10 mM $MgCl_2$, 100 mM $NH_4Cl$, 3% glycerol, 0.05% xylene cyanol). The mixtures were incubated at 37° C. for 20 min and immediately separated on 5% polyacrylamide gels (9 watts). The electrophoresis buffer consisted of 36 mM Tris base, 64 mM HEPES, 0.1 mM EDTA, 10 mM $MgCl_2$ (pH 7.5 without any adjustment). Quantitation of free target RNA and of the complex was performed with a Betascope (Betagen, Waltham, Mass.). The free energies of binding were determined from the equation $\Delta G° = -RT\ \ln(1/Kd)$, where R=0.00198 kcal/mol and T=310.15° K.

The dissociation constants for selected EGSs are shown in Table 2.

TABLE 2

Dissociation constants of EGSs.

| Substrates | Kd (nM) | Km (nM) | Vmax (nmol/min) × 10⁻⁵ | Vmax/Km (nmol/min) × 10⁻⁶ |
|---|---|---|---|---|
| pTyr | | 10 | 2.9 | 2.90 |
| CAT mRNA + $EGS^{CAT}$ | 880 | 120 | 2.9 | 0.24 |
| (Sequence ID No. 8) + $EGS^{CAT}\ \triangle AC$ | 20 | 150 | 11.4 | 0.76 |
| (Sequence ID No. 10) + EGS-5 | 210 | 125 | 16.3 | 1.30 |
| (Sequence ID No. 20) + EGS-8 | 25 | 125 | 21.3 | 1.70 |
| (Sequence ID No. 22) + EGS-9 | 78 | 125 | 30.0 | 2.40 |
| (nucleotides 1–60 of Sequence ID No. 9) + EGS-19 | 710 | 130 | 12.5 | 0.96 |

Table 2 shows the kinetic parameters of EGS-directed cleavage of CAT mRNA in vitro by RNAase P from HeLa cells. $K_d$ refers to measurements of the dissociation constant for binding of EGS to CAT mRNA. The other parameters were determined in standard assays of enzyme kinetics. $V_{max}$ is the value obtained with 0.5 ml (0.6 units) of human RNAase P. pTyr refers to the precursor to $tRNA^{Tyr}$ from E. coli.

The results shown in Table 2 indicate that the $K_d$ values of in vitro selected EGSs are 4 to 40 times lower than that of the parent EGS. Thus, the selected EGSs had higher affinity for the target RNA than did $EGS^{CAT}$. The chimeric substrate derived from clone 9 was cleaved by RNAase P at a rate only about 1.5 times faster than was the target in the mRNA-EGS 9 complex, an indication that the ability of the EGS to bind tightly to the target RNA in solution must be a critical determinant in the efficiency of the substrate complexes.

The differences in $K_d$ values between complexes with $EGS^{CAT}$ (Sequence ID No. 8) and the selected EGSs correspond to the contribution of −1 to −2.4 kcal/mol to the free energy of binding ($\Delta G°$) with selected EGSs ($\Delta G°$) is −8.5 kcal/mol for the complex with $EGS^{CAT}$, −10.1 for the complex with EGS 9 (Sequence ID No. 9) and −10.9 for the complex with $EGS^{CAT}\Delta AC$ (Sequence ID No. 10), thus revealing new interactions in the selected EGS-mRNA complexes.

Deletion of the anticodon stem from $EGS^{CAT}$ resulted in the Kd (for $EGS^{CAT}\Delta AC$) being 44 times lower, and restoration of the stem of EGS 9 (EGS 19) resulted in a $K_d$ that was ten times higher than that for EGS 9 and was close to that of $EGS^{CAT}$ (Table 2). Thus, the intact anticodon stem stabilized a conformation of the EGS that could bind as strongly to the target RNA as does an EGS with no organized anticodon stem. Accordingly, the enhancement of the ability of the selected EGSs for targeting RNA can be assigned, in part, to the increase in the strength of their binding to target RNA.

Cleavage of mRNA directed by the original $EGS^{CAT}$ requires $Mg^{2+}$ ions with an optimum concentration of 25 mM. By contrast, the reaction with certain selected EGSs (EGS 6 (Sequence ID No. 21 and EGS 9 (nucleotides 1 through 60 of Sequence ID No. 9)) proceeds optimally in 2 to 10 mM $Mg^{2+}$ ions. This latter concentration is close to the optimal concentration of $Mg^{2+}$ ions for processing of tRNA precursors by human RNAase P, reported by Doersen et al., *J. Biol. Chem.*, 260: 5942 (1985). Since high concentrations of $Mg^{2+}$ ions are especially effective in the neutralization of repulsion between adjacent regions of the phosphate backbone and the stabilization of RNA folding, the results indicate that the selected EGSs can achieve the appropriate folded structures in the complex with target RNAs without the aid of high concentrations of $Mg^{2+}$ ions.

A kinetic analysis was performed to determine the Michaelis constant ($K_m$) and the maximum velocity ($V_{max}$) of the enzymatic reactions. The cleavage of the precursor to $tRNA^{Tyr}$ from *E. coli* and of CAT mRNA in mRNA-EGS complexes was assayed at various substrate concentrations both above and below the $K_m$ for these substrates. Aliquots were withdrawn from reaction mixtures at regular intervals and analyzed on polyacrylamide-urea gels. Values of $K_m$ and $V_{max}$ were obtained from Lineweaver-Burk double-reciprocal plots. The effective concentrations of substrate used were calculated as the concentration of the complex of target mRNA with EGS as determined from the $K_d$ values shown in Table 2. The $K_m$ for the precursor to $tRNA^{Tyr}$ (pTyr) is 10 nM with human RNAase P, whereas the $K_m$ value of the complex of mRNA-$EGS^{CAT}$ is twelve-fold higher (Table 2). The $K_m$ for all the selected EGSs tested was the same as that of $EGS^{CAT}$. However, the maximum velocities of the reactions with selected EGSs were up to ten times higher than that with the original EGS. Thus, the value of $V_{max}/K_m$ for selected EGSs was increased. The value of $V_{max}/K_m$ of EGS 9, was for example, ten-fold higher than that of $EGS^{CAT}$ and was very close to that of the $tRNA^{Tyr}$ precursor. When the anticodon stem of EGS 9 was restored, however, as it was in EGS 19, $V_{max}$ fell about 2.5-fold, suggesting that the rate of release of the product was specifically reduced by physical interactions of the enzyme with an intact anticodon stem. These data show that the enhanced abilities for targeting of the selected EGSs, as measured in the overall rate of the cleavage reaction, were due to both enhanced affinity of binding to substrate RNAs and to increases in the velocity of the enzymatic reaction.

Example 6

Inhibition of viral mRNA expression with human ribonuclease P.

Herpes simplex virus was used to demonstrate that EGS can be used to target a viral gene in vivo to inhibit viral replication. Herpes simplex viruses are DNA-containing viruses that infect cells, induce synthesis of messenger RNAs, which are transcribed to produce enzymes related to DNA synthesis and breakdown: including thymidine kinase, DNA polymerass and a DNA exonuclease, and viral DNA and viral structural proteins are made and assembled into infectious viral particles. The structure and organization of the herpes simplex virus genome is known, for example, as reported by Roizman, *Cell*, 16, 481–494 (1979). The nucleotide sequence of the thymidine kinase gene of herpes simplex type 1 was described by Wagner, et al., *Proc. Natl. Acad. Sci. USA* 78, 1441–1445 (1981).

Figure 6A:
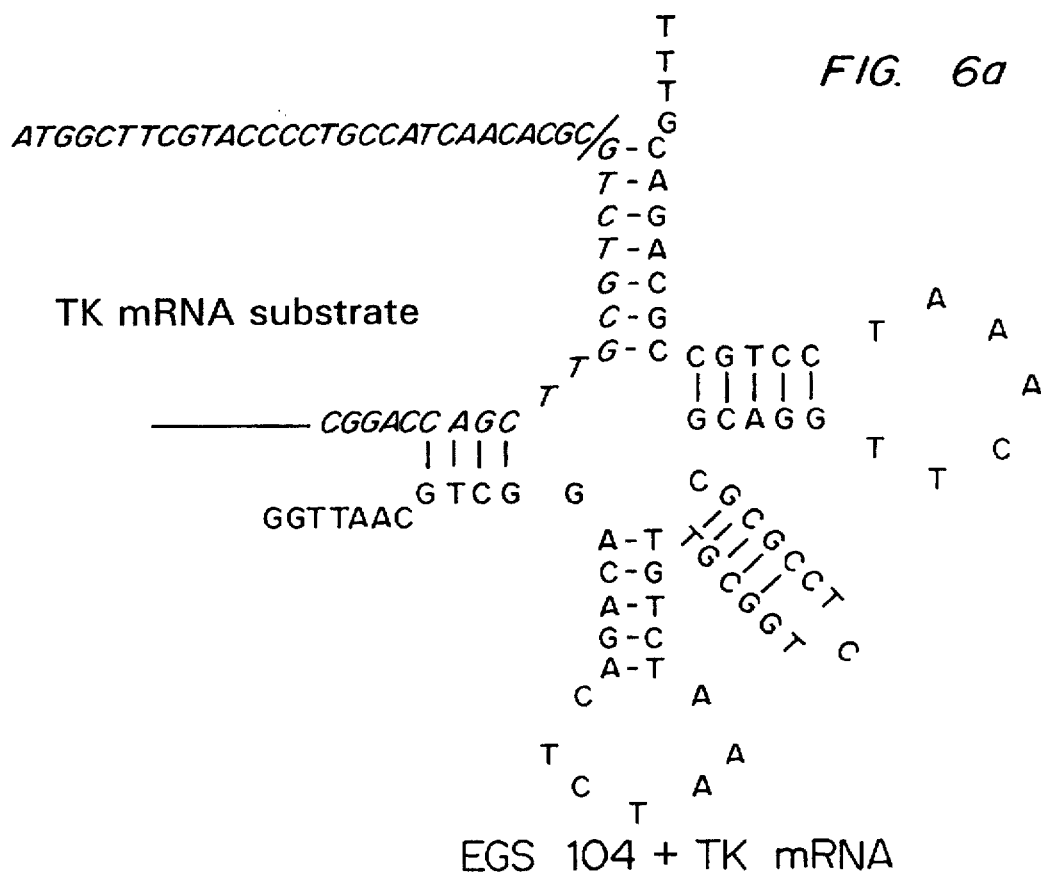
FIGS. 6A, 6B, and 6C are sequence and proposed secondary structures of EGS for herpes simplex virus thymidine kinase mRNA (Sequence ID No. 35)
Figure 6B:
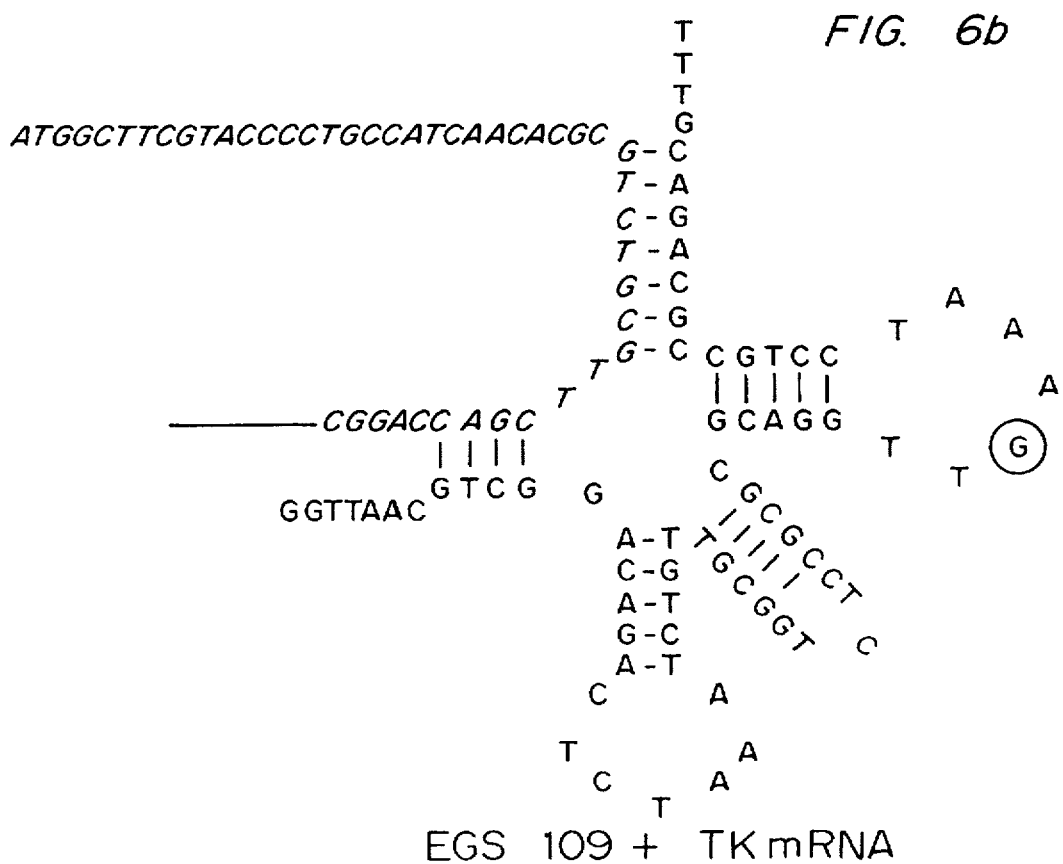
Figure 6C:
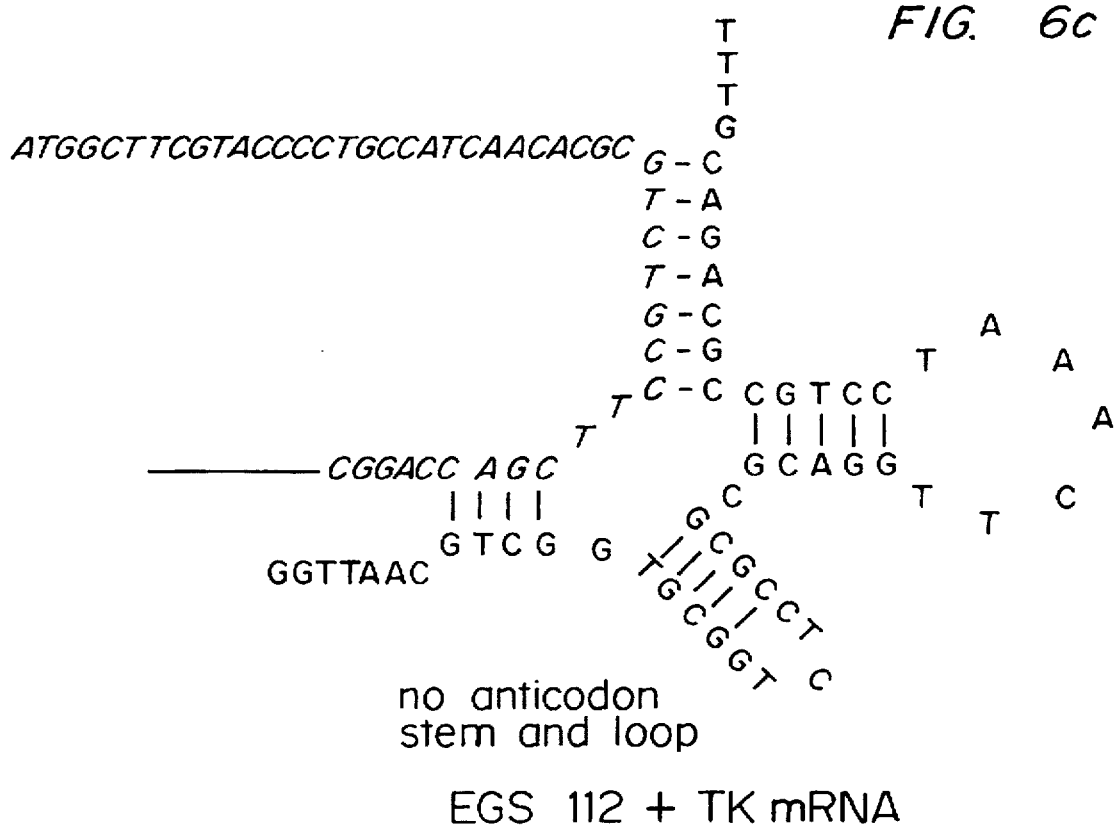

An EGS, shown in FIG. 6A, was designed to target the mRNA encoding thymidine kinass (TK). The target site for RNAase P cleavage is about 25 nucleotides downstream from the TK translation initiation site. An EGS forming an approximately three-fourths-like tRNA was designed and shown in vitro to cleave the TK sequence at the proposed cleavage site. Two other EGSs, which contain a single point mutation in the T-loop (C to G) or deletion of the anti-codon region, shown in FIGS. 6B and 6C, respectively, were constructed based on the results observed in Example 5.

Cell lines and EGS expression vectors were then constructed. Five cell lines were constructed by transfecting plasmid DNAs into human 143TK-cells, which can be obtained from the American Type Culture Collection, Rockville, Md.

Plasmid pFL116 was constructed using pGEM-7Z (Promega, Wis.) and incorporating a gene for neomycin resistance (Neo) (commercially available from Clontech or Stratagene, Calif.). EGS DNA (FIGS. 6A, 6B, and 6C) was digested with KpnI and inserted into the plasmid pmU6(−315/1) (Yuan, et al., *Proc. Natl. Acad. Sci. USA* 89, 8006–8010 (1992) and Das, et al., *EMBO* 7, 503–512 (1988)) at the PsatI (blunted)/KpnI site. This plasmid contains the promoter for the gene for U6 small nuclear RNA, a very strong promoter, and a signal for termination of transcription (T cluster) by RNA polymerase II. EGS plasmids were designated pFL104, pFL109, and pFL112, respectively. The plasmid based on sequence 9 in Table 1 was used as a control.

The cells were stably transfected using a calcium phosphate precipitation method described by Wigler, et al., *Proc. Natl. Acad. Sci. USA* 76, 1373–1376 (1979), with the pFL116 to yield CL116, plasmids EGS 9 and pFL116 to yield CLCAT, plasmids pFL104 and pFL116 to yield CL104, plasmids pFL109 and pFL116 to yield CL109, and plasmids pFL112 and pFL116 to yield CL112, followed by neomycin selection. Cells were cloned, expanded and RNA isolated. Both total and cytoplasmic RNA was isolated and the RNAase protection method described in "Molecular Cloning: A laboratory Manual, Second Edition" Smabrook, Fritsch, and Maniatis, editors, (Cold Spring Harbor Laboratory Press, 1989) at pages 7.71–7.78. This is an extremely sensitive assay where digestion of RNA:RNA hybrids formed using radiolabelled probe is used to assess which cell clones express the EGS.

The results indicated that the EGSs are expressed in both nuclei and cytoplasm.

Cells were then infected with herpes simplex virus using a multiplicity of infection (MOI) of 1 to 1.5 (1 to 1.5 million viral particles/1 million cells) in order to resemble a natural infection with virus. RNA was harvested at 4, 8 and 12 hours post-infection. The internal control probe was used to detect the mRNA levels of HSV α47 and late genes $U_S10$ and $U_S11$. The probe is selected to assure the detection of a high level of viral mRNA expression over the entire cycle of viral infection.

Figure 7:
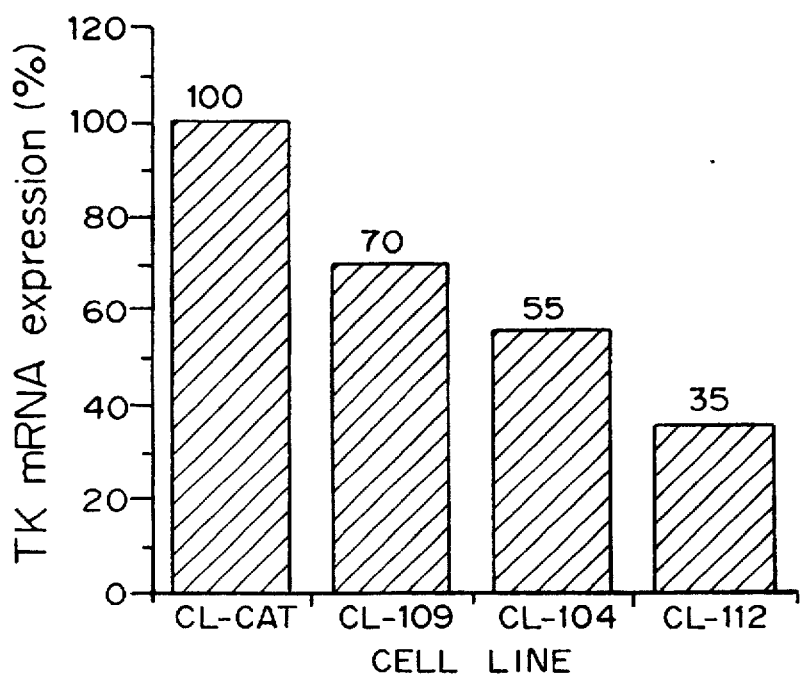
FIG. 7 is a graph of percent TK mRNA expression for cell lines: CL-CAT, CL-109, CL-104, and CL-112.

The results are shown in FIG. 7. TK mRNA expressed was decreased 0% in the control CL-CAT, 30% in CL-109, 45% in CL-104, and 65% in CL-112.

Modifications and variations of the method and compositions to target any RNA for cleavage by eukaryotic RNAase P will be obvious to those skilled in the art from the foregoing detailed description. Such modifications and variations are intended to come within the scope of the appended claims.

---

We claim:

1. A method for selecting a population of external guide sequences for cleavage of a target RNA by RNAase P with increased efficiency over a starting external guide sequence comprising randomizing a section of the starting external guide sequence;

selecting for a subpopulation of the randomized sequences for their ability to be cleaved efficiently by RNAase P;

amplifying those sequences cleaving more efficiently than the starting external guide sequence; and repeating the selection and amplification steps.

2. A method for identifying a population of external guide sequences that promote cleavage of a target RNA by RNAase P with increased efficiency over a starting external guide sequence comprising providing a starting chimeric substrate comprising an external guide sequence portion and a target portion, wherein the external guide sequence portion comprises the nucleotide sequence of the starting external guide sequence, and wherein the chimeric substrate can be cleaved by RNAase P;

randomizing a section of the external guide sequence portion of the starting chimeric substrate, resulting in a population of randomized chimeric substrates;

selecting for a subpopulation of the randomized chimeric substrates for their ability to be cleaved efficiently by RNAase P;

amplifying the selected subpopulation of randomized chimeric substrates; and repeating the selection and amplification steps;

wherein the external guide sequence portions of the selected subpopulation of randomized chimeric substrates represent the population of external guide sequences that promote cleavage of a target RNA by RNAase P with increased efficiency over a starting external guide sequence.

3. A method for identifying a population of external guide sequences that promote cleavage of a target RNA by RNAase P with increased efficiency over a starting external guide sequence comprising (a) providing a starting chimeric substrate comprising an external guide sequence portion and a target portion, wherein the external guide sequence portion comprises the nucleotide sequence of the starting external guide sequence, and wherein the chimeric substrate can be cleaved by RNAase P;

(b) randomizing a section of the external guide sequence portion of the starting chimeric substrate, resulting in a population of randomized chimeric substrates; and (c) selecting for a subpopulation of the randomized chimeric substrates for their ability to be cleaved efficiently by RNAase P;

wherein the external guide sequence portions of the selected subpopulation of randomized chimeric substrates represent the population of external guide sequences that promote cleavage of a target RNA by RNAase P with increased efficiency over a starting external guide sequence.

4. The method of claim 3 further comprising, following step (c), (d) amplifying the selected subpopulation of randomized chimeric substrates; and (e) selecting for a subpopulation of the randomized chimeric substrates for their ability to be cleaved efficiently by RNAase P.

5. The method of claim 4 further comprising, following step (e), (f) repeating steps (d) and (e) one or more times.

6. The method of claim 3 further comprising, following step (c), (d) amplifying the selected subpopulation of randomized chimeric substrates; and (e) repeating step (c).

7. (New) The method of claim 6 further comprising, following step (e), (f) repeating steps (d) and (e) one or more times.

* * * * *

SEQUENCE LISTING ( 1 ) GENERAL INFORMATION:

( i i i ) NUMBER OF SEQUENCES: 39

( 2 ) INFORMATION FOR SEQ ID NO:1:

( i ) SEQUENCE CHARACTERISTICS:
        ( A ) LENGTH: 88 base pairs
        ( B ) TYPE: nucleic acid
        ( C ) STRANDEDNESS: single
        ( D ) TOPOLOGY: linear ( i i ) MOLECULE TYPE: RNA (genomic)

( i i i ) HYPOTHETICAL: NO ( i v ) ANTI-SENSE: NO ( x i ) SEQUENCE DESCRIPTION: SEQ ID NO:1:

GAACAUUUUG AGGCAUUUCA GUCAGUUGGC CAAACUGAGC AGACUCUAAA UCUGCNNNNN 60

GAAGGUUCNN NNCCUUCAUG CCUCACCA 88

( 2 ) INFORMATION FOR SEQ ID NO:2:

( i ) SEQUENCE CHARACTERISTICS:
        ( A ) LENGTH: 61 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:2:

TAATACGACT CACTATAGAA CATTTGAGG CATTTCAGTC AGTTGGCCAA ACTGAGCAGA 60

C 61

( 2 ) INFORMATION FOR SEQ ID NO:3:

( i ) SEQUENCE CHARACTERISTICS:
        ( A ) LENGTH: 61 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

TGGTGAGGCA TGAAGGNNNN GAACCTTCNN NNNGCAGATT TAGAGTCTGC TCAGTTGGC 60

C 61

( 2 ) INFORMATION FOR SEQ ID NO:4:

( i ) SEQUENCE CHARACTERISTICS:
    ( A ) LENGTH: 99 base pairs
    ( B ) TYPE: nucleic acid
    ( C ) STRANDEDNESS: single
    ( D ) TOPOLOGY: linear ( i i ) MOLECULE TYPE: tRNA ( i i i ) HYPOTHETICAL: NO ( i v ) ANTI-SENSE: NO ( x i ) SEQUENCE DESCRIPTION: SEQ ID NO:4:

```
GAAUACACGG AAUUGGUGGG GUUCCCGAGC GGCCAAAGGG AGCAGACUCU AAAUCUGCCG      60
UCAUCGACUU CGAAGGUUCG AAUCCUUCCC CCACUGCCA                             99
```

( 2 ) INFORMATION FOR SEQ ID NO:5:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: tRNA ( i i i ) HYPOTHETICAL: NO ( i v ) ANTI-SENSE: NO ( x i ) SEQUENCE DESCRIPTION: SEQ ID NO:5:

```
GCCAAGGGA GCAGACUCUA AAUCUGCCGU CAUCGACUUC GAAGGUUCGA AUCCUUCCC        60
CACCACCAUC A                                                          71
```

( 2 ) INFORMATION FOR SEQ ID NO:6:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: tRNA ( i i i ) HYPOTHETICAL: NO ( i v ) ANTI-SENSE: NO ( x i ) SEQUENCE DESCRIPTION: SEQ ID NO:6:

```
GAAUACACGG AAUUGGUGGG GUUCCCGA                                         28
```

( 2 ) INFORMATION FOR SEQ ID NO:7:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: mRNA ( i i i ) HYPOTHETICAL: NO ( i v ) ANTI-SENSE: NO ( x i ) SEQUENCE DESCRIPTION: SEQ ID NO:7:

```
AUGGAACAUU UUGAGGCAUU UCAGUCAGUU UAA                                   33
```

( 2 ) INFORMATION FOR SEQ ID NO:8:

( i ) SEQUENCE CHARACTERISTICS:
    ( A ) LENGTH: 70 base pairs
    ( B ) TYPE: nucleic acid
    ( C ) STRANDEDNESS: single
    ( D ) TOPOLOGY: linear ( i i ) MOLECULE TYPE: tRNA ( i i i ) HYPOTHETICAL: NO ( i v ) ANTI-SENSE: NO ( x i ) SEQUENCE DESCRIPTION: SEQ ID NO:8:

GGCCAAACUG AGCAGACUCU AAAUCUGCCG UCAUCGACUU CGAAGGUUCG AAUCCUUCAU    60

GCCUCACCAU    70

( 2 ) INFORMATION FOR SEQ ID NO:9:

( i ) SEQUENCE CHARACTERISTICS:
    ( A ) LENGTH: 61 base pairs
    ( B ) TYPE: nucleic acid
    ( C ) STRANDEDNESS: single
    ( D ) TOPOLOGY: linear ( i i ) MOLECULE TYPE: tRNA ( i i i ) HYPOTHETICAL: NO ( i v ) ANTI-SENSE: NO ( x i ) SEQUENCE DESCRIPTION: SEQ ID NO:9:

GGCCAAACUG AGCAGACUCU AAAUCGCAAA CGGAAGGUUC GUGCCCUUCA UGCCUCACCA    60

U    61

( 2 ) INFORMATION FOR SEQ ID NO:10:

( i ) SEQUENCE CHARACTERISTICS:
    ( A ) LENGTH: 53 base pairs
    ( B ) TYPE: nucleic acid
    ( C ) STRANDEDNESS: single
    ( D ) TOPOLOGY: linear ( i i ) MOLECULE TYPE: tRNA ( i i i ) HYPOTHETICAL: NO ( i v ) ANTI-SENSE: NO ( x i ) SEQUENCE DESCRIPTION: SEQ ID NO:10:

GGCCAAACUG ACGUCAUCGA CUUCGAAGGU UCGAAUCCUU CAUGCCUCAC CAU    53

( 2 ) INFORMATION FOR SEQ ID NO:11:

( i ) SEQUENCE CHARACTERISTICS:
    ( A ) LENGTH: 340 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x ) PUBLICATION INFORMATION:
    ( A ) AUTHORS: Baer,
    ( C ) JOURNAL: Nucleic Acids Res.
    ( D ) VOLUME: 18

(F) PAGES: 97-103
(G) DATE: 1989
(K) RELEVANT RESIDUES IN SEQ ID NO:1: FROM 1 TO 340

(xi) SEQUENCE DESCRIPTION: SEQ ID NO:11:

| | | | | | | |
|---|---|---|---|---|---|---|
| ATGGGCGGAG | GGAAGCTCAT | CAGTGGGGCC | ACGAGCTGAG | TGCGTCCTGT | CACTCCACTC | 60 |
| CCATGTCCCT | TGGGAAGGTC | TGAGACTAGG | GCCAGAGGCG | GCCCTAACAG | GGCTCTCCCT | 120 |
| GAGCTTCAGG | GAGGTGAGTT | CCCAGAGAAC | GGGGCTCCGC | GCGAGGTCAG | ACTGGGCAGG | 180 |
| AGATGCCGTG | GACCCCGCCC | TTCGGGGAGG | GGCCCGGCGG | ATGCCTCCTT | TGCCGGAGCT | 240 |
| TGGAACAGAC | TCACGGCCAG | CGAAGTGAGT | TCAATGGCTG | AGGTGAGGTA | CCCCGCAGGG | 300 |
| GACCTCATAA | CCCAATTCAG | ACCACTCTCC | TCCGCCCATT | | | 340 |

(2) INFORMATION FOR SEQ ID NO:12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:12:

GCCAAACTGA GCAGACTC        18

(2) INFORMATION FOR SEQ ID NO:13:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:13:

GCGCGGTACC AAAAATGGTG AGGCATGAAG G        31

(2) INFORMATION FOR SEQ ID NO:14:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:14:

GGCCGTAATA TCCAGCTGAA CGG        23

(2) INFORMATION FOR SEQ ID NO:15:

(i) SEQUENCE CHARACTERISTICS:
        (A) LENGTH: 16 base pairs ( B ) TYPE: nucleic acid
                    ( C ) STRANDEDNESS: single
                    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:15:

TGGTGAGGCA TGAAGG         16

( 2 ) INFORMATION FOR SEQ ID NO:16:

( i ) SEQUENCE CHARACTERISTICS:
                    ( A ) LENGTH: 33 base pairs
                    ( B ) TYPE: nucleic acid
                    ( C ) STRANDEDNESS: single
                    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:16:

TAATACGACT CACTATAGGC CAACTGAGCA GAC         33

( 2 ) INFORMATION FOR SEQ ID NO:17:

( i ) SEQUENCE CHARACTERISTICS:
                    ( A ) LENGTH: 61 base pairs
                    ( B ) TYPE: nucleic acid
                    ( C ) STRANDEDNESS: single
                    ( D ) TOPOLOGY: linear ( i i ) MOLECULE TYPE: tRNA ( i i i ) HYPOTHETICAL: NO ( i v ) ANTI-SENSE: NO ( x i ) SEQUENCE DESCRIPTION: SEQ ID NO:17:

GGCCAAACUG AGCAGACUCU AAAUCGGCCC UUCGAAGGUU CGCCCCUUC AUGCCUCACC         60

A         61

( 2 ) INFORMATION FOR SEQ ID NO:18:

( i ) SEQUENCE CHARACTERISTICS:
                    ( A ) LENGTH: 62 base pairs
                    ( B ) TYPE: nucleic acid
                    ( C ) STRANDEDNESS: single
                    ( D ) TOPOLOGY: linear ( i i ) MOLECULE TYPE: tRNA ( i i i ) HYPOTHETICAL: NO ( i v ) ANTI-SENSE: NO ( x i ) SEQUENCE DESCRIPTION: SEQ ID NO:18:

GGCCAAACUG AGCAGACUCU AAAUCUGCAC GAGAGAAGGU UCGUGCCCUU CAUGCCUCAC         60

CA         62

( 2 ) INFORMATION FOR SEQ ID NO:19:

( i ) SEQUENCE CHARACTERISTICS:
                    ( A ) LENGTH: 61 base pairs ( B ) TYPE: nucleic acid
( C ) STRANDEDNESS: single
( D ) TOPOLOGY: linear ( i i ) MOLECULE TYPE: tRNA ( i i i ) HYPOTHETICAL: NO ( i v ) ANTI-SENSE: NO ( x i ) SEQUENCE DESCRIPTION: SEQ ID NO:19:

GGCCAAACUG AGCAGACUCU AAACUGGCCU AACGAAGGUU CGCCCCCUUC AUGCCUCACC  60
A  61

( 2 ) INFORMATION FOR SEQ ID NO:20:

( i ) SEQUENCE CHARACTERISTICS:
( A ) LENGTH: 60 base pairs
( B ) TYPE: nucleic acid
( C ) STRANDEDNESS: single
( D ) TOPOLOGY: linear ( i i ) MOLECULE TYPE: tRNA ( i i i ) HYPOTHETICAL: NO ( i v ) ANTI-SENSE: NO ( x i ) SEQUENCE DESCRIPTION: SEQ ID NO:20:

GGCCAAACUG AGCAGACUCU AAAUUGCCCA ACGAAGGUUC ACCCCCUUCA UGCCUCACCA  60

( 2 ) INFORMATION FOR SEQ ID NO:21:

( i ) SEQUENCE CHARACTERISTICS:
( A ) LENGTH: 59 base pairs
( B ) TYPE: nucleic acid
( C ) STRANDEDNESS: single
( D ) TOPOLOGY: linear ( i i ) MOLECULE TYPE: tRNA ( i i i ) HYPOTHETICAL: NO ( i v ) ANTI-SENSE: NO ( x i ) SEQUENCE DESCRIPTION: SEQ ID NO:21:

GGCCAAACUG AGCAGACUCC AAAUCCACCA AGAAGGUUCG UGCCCUUCAU GCCUCACCA  59

( 2 ) INFORMATION FOR SEQ ID NO:22:

( i ) SEQUENCE CHARACTERISTICS:
( A ) LENGTH: 60 base pairs
( B ) TYPE: nucleic acid
( C ) STRANDEDNESS: single
( D ) TOPOLOGY: linear ( i i ) MOLECULE TYPE: tRNA ( i i i ) HYPOTHETICAL: NO ( i v ) ANTI-SENSE: NO ( x i ) SEQUENCE DESCRIPTION: SEQ ID NO:22:

GGCCAAACUG AGCAGACUCU AAACUCCUCC CAGAAGGUUC GUGCCCUUCA UGCCUCACCA  60

( 2 ) INFORMATION FOR SEQ ID NO:23:

( i ) SEQUENCE CHARACTERISTICS:
( A ) LENGTH: 61 base pairs
( B ) TYPE: nucleic acid
( C ) STRANDEDNESS: single (D) TOPOLOGY: linear (ii) MOLECULE TYPE: tRNA (iii) HYPOTHETICAL: NO (iv) ANTI-SENSE: NO (xi) SEQUENCE DESCRIPTION: SEQ ID NO:23:

GGCCAAACUG AGCAGACUCU AAAUCGGCCU ACGGAAGGUU CGCCCCUUC AUGCCUCACC 60

A 61

(2) INFORMATION FOR SEQ ID NO:24:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: tRNA (iii) HYPOTHETICAL: NO (iv) ANTI-SENSE: NO (xi) SEQUENCE DESCRIPTION: SEQ ID NO:24:

GGCCAAACUG AGCAGACGCU AAAUCUACCC CGUGAAGGUU CGUCCCUUC AUGCCUCACC 60

A 61

(2) INFORMATION FOR SEQ ID NO:25:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: tRNA (iii) HYPOTHETICAL: NO (iv) ANTI-SENSE: NO (xi) SEQUENCE DESCRIPTION: SEQ ID NO:25:

GGCCAAACUG AGCAGACUCU AAAUUUGCCA CCAGAAGGUU CGCCCCUUC AUGCCUCACC 60

A 61

(2) INFORMATION FOR SEQ ID NO:26:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: tRNA (iii) HYPOTHETICAL: NO (iv) ANTI-SENSE: NO (xi) SEQUENCE DESCRIPTION: SEQ ID NO:26:

GGCCAAACUG AGCAGACUCA AAUCUGGCCA UUCGAAGGUU CGCCCCUUC AUGCCUCACC 60

A 61

(2) INFORMATION FOR SEQ ID NO:27:

( i ) SEQUENCE CHARACTERISTICS:
    ( A ) LENGTH: 60 base pairs
    ( B ) TYPE: nucleic acid
    ( C ) STRANDEDNESS: single
    ( D ) TOPOLOGY: linear ( i i ) MOLECULE TYPE: tRNA ( i i i ) HYPOTHETICAL: NO ( i v ) ANTI-SENSE: NO ( x i ) SEQUENCE DESCRIPTION: SEQ ID NO:27:

```
GGCCAAACUG AGCAGACUCU AAAUCGCAGU GUGAAGGUUC GUGCCCUUCA UGCCUCACCA      60
```

( 2 ) INFORMATION FOR SEQ ID NO:28:

( i ) SEQUENCE CHARACTERISTICS:
    ( A ) LENGTH: 61 base pairs
    ( B ) TYPE: nucleic acid
    ( C ) STRANDEDNESS: single
    ( D ) TOPOLOGY: linear ( i i ) MOLECULE TYPE: tRNA ( i i i ) HYPOTHETICAL: NO ( i v ) ANTI-SENSE: NO ( x i ) SEQUENCE DESCRIPTION: SEQ ID NO:28:

```
GGCCAAACUG AGCAGACUCU AAAUCAGCGC GUGGAAGGUU CGUGCCCUUC AUGCCUCACC      60
A                                                                      61
```

( 2 ) INFORMATION FOR SEQ ID NO:29:

( i ) SEQUENCE CHARACTERISTICS:
    ( A ) LENGTH: 61 base pairs
    ( B ) TYPE: nucleic acid
    ( C ) STRANDEDNESS: single
    ( D ) TOPOLOGY: linear ( i i ) MOLECULE TYPE: tRNA ( i i i ) HYPOTHETICAL: NO ( i v ) ANTI-SENSE: NO ( x i ) SEQUENCE DESCRIPTION: SEQ ID NO:29:

```
GGCCAAACUG AGCAGACUCU AAAUCGGCCG CACGAAGGUU CGCCCCUUC AUGCCUCACC       60
A                                                                      61
```

( 2 ) INFORMATION FOR SEQ ID NO:30:

( i ) SEQUENCE CHARACTERISTICS:
    ( A ) LENGTH: 61 base pairs
    ( B ) TYPE: nucleic acid
    ( C ) STRANDEDNESS: single
    ( D ) TOPOLOGY: linear ( i i ) MOLECULE TYPE: tRNA ( i i i ) HYPOTHETICAL: NO ( i v ) ANTI-SENSE: NO ( x i ) SEQUENCE DESCRIPTION: SEQ ID NO:30:

```
GGCCAAACUG AGCAGACACU AAAUUUGCAC GAGGAAGGUU CGCCCCCUUC AUGCCUCACC      60
A                                                                      61
```

(2) INFORMATION FOR SEQ ID NO:31:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: tRNA (iii) HYPOTHETICAL: NO (iv) ANTI-SENSE: NO (xi) SEQUENCE DESCRIPTION: SEQ ID NO:31:

GGCCAAACUG AGCAGACCCU AAAUCUGCCC CCGGAAGGUU CGUGCCCUUC AUGCCUCACC     60

A     61

(2) INFORMATION FOR SEQ ID NO:32:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:32:

GCCAAACTGA CGTCATCGAC TTCG     24

(2) INFORMATION FOR SEQ ID NO:33:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:33:

AACAGCTATG ACCATG     16

(2) INFORMATION FOR SEQ ID NO:34:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:34:

GTAATACGAC TCACTATAGG CCAAACTGAG CAGACTCTAA ATCTGCAAAC GGAAGGTTC     59

(2) INFORMATION FOR SEQ ID NO:35:

( i ) SEQUENCE CHARACTERISTICS:
    ( A ) LENGTH: 47 base pairs
    ( B ) TYPE: nucleic acid
    ( C ) STRANDEDNESS: single
    ( D ) TOPOLOGY: linear ( i i ) MOLECULE TYPE: tRNA ( i i i ) HYPOTHETICAL: NO ( i v ) ANTI-SENSE: NO ( x i ) SEQUENCE DESCRIPTION: SEQ ID NO:35:

ATGGCTTCGT ACCCCTGCCA TCAACACGCG TCTGCGTTCG ACCAGGC    47

( 2 ) INFORMATION FOR SEQ ID NO:36:

( i ) SEQUENCE CHARACTERISTICS:
    ( A ) LENGTH: 71 base pairs
    ( B ) TYPE: nucleic acid
    ( C ) STRANDEDNESS: single
    ( D ) TOPOLOGY: linear ( i i ) MOLECULE TYPE: tRNA ( i i i ) HYPOTHETICAL: NO ( i v ) ANTI-SENSE: NO ( x i ) SEQUENCE DESCRIPTION: SEQ ID NO:36:

GGTTAACGTC GGACAGACTC TAAATCTGTT GCGGTCTCCG CGCGCAGGTT CAAATCCTGC    60

CGCAGACGTT T    71

( 2 ) INFORMATION FOR SEQ ID NO:37:

( i ) SEQUENCE CHARACTERISTICS:
    ( A ) LENGTH: 71 base pairs
    ( B ) TYPE: nucleic acid
    ( C ) STRANDEDNESS: single
    ( D ) TOPOLOGY: linear ( i i ) MOLECULE TYPE: tRNA ( i i i ) HYPOTHETICAL: NO ( i v ) ANTI-SENSE: NO ( x i ) SEQUENCE DESCRIPTION: SEQ ID NO:37:

GGTTAACGTC GGACAGACTC TAAATCTGTT GCGGTCTCCG CGCGCAGGTT GAAATCCTGC    60

CGCAGACGTT T    71

( 2 ) INFORMATION FOR SEQ ID NO:38:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( i i ) MOLECULE TYPE: tRNA ( i i i ) HYPOTHETICAL: NO ( i v ) ANTI-SENSE: NO ( x i ) SEQUENCE DESCRIPTION: SEQ ID NO:38:

GGTTAACGTC GGTGCGGTCT CCGCGCGCAG GTTCAAATCC TGCCGCAGAC GTTT    54

( 2 ) INFORMATION FOR SEQ ID NO:39:

(i) SEQUENCE CHARACTERISTICS:
  (A) LENGTH: 62 base pairs
  (B) TYPE: nucleic acid
  (C) STRANDEDNESS: single
  (D) TOPOLOGY: linear (ii) MOLECULE TYPE: tRNA (iii) HYPOTHETICAL: NO (iv) ANTI-SENSE: NO (xi) SEQUENCE DESCRIPTION: SEQ ID NO:39:

GGCCAAACUG AGCAGACUCU AAAUCUGCAA ACGGAAGGUU CGUGCCCUUC AUGCCUCACC    60

AU    62